(12) United States Patent
Leung et al.

(10) Patent No.: US 10,610,297 B2
(45) Date of Patent: *Apr. 7, 2020

(54) ELECTROSURGICAL TISSUE TREATMENT DEVICE

(71) Applicant: Avent, Inc., Alpharetta, GA (US)

(72) Inventors: Mark Leung, Toronto (CA); Krishan Shah, Mississauga (CA); Laura Conquergood, Mississauga (CA); Subashini Chandran, Toronto (CA); Neil Godara, Milton (CA)

(73) Assignee: Avent, Inc., Alpharetta, GA (US)

(*) Notice: Subject to any disclaimer, the term of this patent is extended or adjusted under 35 U.S.C. 154(b) by 153 days.

This patent is subject to a terminal disclaimer.

(21) Appl. No.: 15/285,075

(22) Filed: Oct. 4, 2016

(65) Prior Publication Data
US 2017/0020606 A1 Jan. 26, 2017

Related U.S. Application Data

(60) Continuation of application No. 14/145,429, filed on Dec. 31, 2013, now Pat. No. 9,474,573, which is a
(Continued)

(51) Int. Cl.
*A61B 18/12* (2006.01)
*A61B 18/18* (2006.01)
(Continued)

(52) U.S. Cl.
CPC ............ *A61B 18/18* (2013.01); *A61B 18/148* (2013.01); *A61B 2018/00023* (2013.01); *A61B 2018/0044* (2013.01); *A61B 2018/00875* (2013.01)

(58) Field of Classification Search
CPC .................. A61B 18/18; A61B 18/148; A61B 2018/00023; A61B 2018/0044; A61B 2018/00875
(Continued)

(56) References Cited

U.S. PATENT DOCUMENTS 2,526,662 A 10/1950 Hipps et al.
3,477,423 A 11/1969 Griffith
(Continued)

FOREIGN PATENT DOCUMENTS

EP 0438242 1/1991
EP 996920 5/2000
(Continued)

OTHER PUBLICATIONS

Amorettia et al., "Preliminary Communication on a Decompression Probe (Dekompressor1) in Percutaneous Discectomy. Ten Case Reports", Journal of Clinical Imaging 26 (2005) 98-101.
(Continued)

*Primary Examiner* — Aaron F Roane
(74) *Attorney, Agent, or Firm* — Dority & Manning, P.A.

(57) ABSTRACT

A device for treating spinal tissue of a patient's body may include an energy source and first and second probe assemblies. Each of the probe assemblies may have an electrically conductive energy delivery device electrically coupled to the energy source, and may also have an electrothermal device for cooling the probe assembly. The device is configured so that the energy source delivers energy to the spinal tissue through the energy delivery devices in a bipolar mode that concentrates delivered energy between the energy delivery devices to create a lesion within the spinal tissue while the electrothermal devices cool the probe assemblies. Related methods of use include cooling, at times via an electrothermal device.

18 Claims, 10 Drawing Sheets

Related U.S. Application Data division of application No. 13/964,460, filed on Aug. 12, 2013, now Pat. No. 8,740,897, which is a continuation of application No. 11/939,280, filed on Nov. 13, 2007, now Pat. No. 8,518,036, which is a continuation of application No. 11/105,524, filed on Apr. 14, 2005, now Pat. No. 7,294,127, which is a continuation-in-part of application No. 10/087,856, filed on Mar. 5, 2002, now Pat. No. 6,896,675.

(51) Int. Cl.
*A61B 18/14* (2006.01)
*A61B 18/00* (2006.01)

(58) Field of Classification Search
USPC .......................................................... 606/41
See application file for complete search history.

(56) References Cited

U.S. PATENT DOCUMENTS

| | | | |
|---|---|---|---|
| 3,732,858 A | 5/1973 | Banko | |
| 3,774,612 A | 11/1973 | Marco | |
| 4,177,797 A | 12/1979 | Baylis et al. | |
| 4,369,788 A | 1/1983 | Goald | |
| 4,411,266 A | 10/1983 | Cosman | |
| 4,512,344 A | 4/1985 | Barber | |
| 4,600,014 A | 7/1986 | Beraha | |
| 4,649,919 A | 3/1987 | Thimsen et al. | |
| 4,699,154 A | 10/1987 | Lindgren | |
| 4,834,729 A | 5/1989 | Sjostrom | |
| 4,857,046 A | 8/1989 | Stevens et al. | |
| 4,883,458 A | 11/1989 | Shiber | |
| 4,907,589 A | 3/1990 | Cosman | |
| 4,958,625 A | 9/1990 | Bates et al. | |
| 4,979,939 A | 12/1990 | Shiber | |
| 5,002,553 A | 3/1991 | Shiber | |
| 5,027,792 A | 7/1991 | Meyer | |
| 5,074,841 A | 12/1991 | Ademovic et al. | |
| 5,084,052 A | 1/1992 | Jacobs | |
| RE34,056 E | 9/1992 | Lindgren | |
| 5,167,658 A | 12/1992 | Ensslin | |
| 5,183,054 A | 2/1993 | Burkholder et al. | |
| 5,201,729 A | 4/1993 | Hertzmann et al. | |
| 5,233,515 A | 8/1993 | Cosman | |
| 5,234,000 A | 8/1993 | Hakky et al. | |
| 5,277,201 A | 1/1994 | Stern | |
| 5,334,193 A | 8/1994 | Nardella | |
| 5,342,357 A | 8/1994 | Nardella | |
| 5,383,874 A | 1/1995 | Jackson et al. | |
| 5,383,884 A | 1/1995 | Summers | |
| 5,423,799 A | 6/1995 | Shiu | |
| 5,423,807 A | 6/1995 | Milder | |
| 5,423,811 A | 6/1995 | Imran et al. | |
| 5,433,739 A | 7/1995 | Sluijter et al. | |
| 5,437,662 A | 8/1995 | Nardella | |
| 5,458,596 A | 10/1995 | Lax et al. | |
| 5,484,400 A | 1/1996 | Edwards et al. | |
| 5,486,161 A | 1/1996 | Lax et al. | |
| 5,520,682 A | 5/1996 | Baust et al. | |
| 5,536,267 A | 7/1996 | Edwards et al. | |
| 5,546,161 A | 8/1996 | Sakai et al. | |
| 5,569,242 A | 10/1996 | Lax et al. | |
| 5,569,284 A | 10/1996 | Young et al. | |
| 5,571,147 A | 11/1996 | Sluijter et al. | |
| 5,574,117 A | 11/1996 | Yoshida et al. | |
| 5,591,187 A | 1/1997 | Dekel | |
| 5,599,346 A | 2/1997 | Edwards et al. | |
| 5,603,221 A | 2/1997 | Maytal | |
| 5,647,871 A | 7/1997 | Levine et al. | |
| 5,651,780 A | 7/1997 | Jackson et al. | |
| 5,658,278 A | 8/1997 | Imran et al. | |
| 5,688,267 A | 11/1997 | Panescu et al. | |
| 5,697,927 A | 12/1997 | Imran et al. | |
| 5,718,701 A | 2/1998 | Shai et al. | |
| 5,735,847 A | 4/1998 | Gough et al. | |
| 5,785,705 A | 7/1998 | Baker | |
| 5,800,481 A | 9/1998 | Loos | |
| 5,810,804 A | 9/1998 | Gough et al. | |
| 5,873,882 A | 2/1999 | Straub et al. | |
| 5,876,414 A | 3/1999 | Straub | |
| 5,906,612 A | 5/1999 | Chinn | |
| 5,913,859 A | 6/1999 | Shapira | |
| 5,916,163 A | 6/1999 | Panescu et al. | |
| 5,928,159 A * | 7/1999 | Eggers | A61B 5/0531 600/373 |
| 5,957,922 A | 9/1999 | Imran | |
| 5,957,961 A | 9/1999 | Maguire et al. | |
| 5,968,062 A | 10/1999 | Thomas et al. | |
| 5,971,980 A | 10/1999 | Sherman | |
| 5,980,504 A | 11/1999 | Sharkey et al. | |
| 5,983,141 A | 11/1999 | Sluijter et al. | |
| 6,007,570 A | 12/1999 | Sharkey et al. | |
| 6,015,407 A | 1/2000 | Rieb et al. | |
| 6,016,809 A | 1/2000 | Mulier et al. | |
| 6,024,751 A | 2/2000 | Lovato et al. | |
| 6,032,673 A | 3/2000 | Savage et al. | |
| 6,033,399 A | 3/2000 | Gines | |
| 6,035,238 A | 3/2000 | Ingle et al. | |
| 6,051,019 A | 4/2000 | Dobak, III | |
| 6,053,912 A | 4/2000 | Panescu et al. | |
| 6,053,937 A | 4/2000 | Edwards et al. | |
| 6,063,085 A | 5/2000 | Tay et al. | |
| 6,073,051 A | 6/2000 | Sharkey et al. | |
| 6,074,386 A | 6/2000 | Goble et al. | |
| 6,074,389 A | 6/2000 | Levine et al. | |
| 6,074,412 A | 6/2000 | Mikus et al. | |
| 6,083,237 A | 7/2000 | Huitema et al. | |
| 6,095,149 A | 8/2000 | Sharkey et al. | |
| 6,099,514 A | 8/2000 | Sharkey et al. | |
| 6,102,046 A * | 8/2000 | Weinstein | A61M 25/0133 128/898 |
| 6,109,268 A | 8/2000 | Thapliyal et al. | |
| 6,113,595 A | 9/2000 | Muntermann | |
| 6,122,549 A | 9/2000 | Sharkey et al. | |
| 6,123,702 A | 9/2000 | Swanson et al. | |
| 6,126,682 A | 10/2000 | Sharkey et al. | |
| 6,136,014 A | 10/2000 | Sirimanne et al. | |
| 6,139,545 A | 10/2000 | Utley et al. | |
| 6,146,380 A | 11/2000 | Racz et al. | |
| 6,161,048 A | 12/2000 | Sluijter et al. | |
| 6,183,468 B1 | 2/2001 | Swanson et al. | |
| 6,197,021 B1 | 3/2001 | Panescu et al. | |
| 6,206,876 B1 | 3/2001 | Levine et al. | |
| 6,217,573 B1 | 4/2001 | Webster | |
| 6,228,080 B1 | 5/2001 | Gines | |
| 6,228,081 B1 | 5/2001 | Goble | |
| 6,237,569 B1 | 5/2001 | Stelzer et al. | |
| 6,238,387 B1 | 5/2001 | Miller, III | |
| 6,241,725 B1 | 6/2001 | Cosman | |
| 6,246,912 B1 | 6/2001 | Sluijter et al. | |
| 6,258,086 B1 | 7/2001 | Ashlet et al. | |
| 6,259,952 B1 | 7/2001 | Sluijter et al. | |
| 6,261,311 B1 | 7/2001 | Sharket et al. | |
| 6,264,650 B1 | 7/2001 | Hovda et al. | |
| 6,264,651 B1 | 7/2001 | Underwood et al. | |
| 6,273,861 B1 | 8/2001 | Bates et al. | |
| 6,277,112 B1 | 8/2001 | Underwood et al. | |
| 6,283,960 B1 | 9/2001 | Ashley | |
| 6,283,961 B1 | 9/2001 | Underwood et al. | |
| 6,290,715 B1 | 9/2001 | Sharkey et al. | |
| 6,293,943 B1 | 9/2001 | Panescu et al. | |
| 6,296,636 B1 | 10/2001 | Cheng et al. | |
| 6,309,387 B1 | 10/2001 | Eggers et al. | |
| 6,312,428 B1 | 11/2001 | Eggers et al. | |
| 6,325,806 B1 | 12/2001 | Fox | |
| 6,355,031 B1 | 3/2002 | Edwards et al. | |
| 6,355,032 B1 | 3/2002 | Hovda et al. | |
| 6,379,348 B1 | 4/2002 | Onik | |
| 6,391,026 B1 | 5/2002 | Hung et al. | |
| 6,416,508 B1 | 7/2002 | Eggers et al. | |
| 6,432,103 B1 | 8/2002 | Ellsberry et al. | |
| 6,451,015 B1 | 9/2002 | Rittman, III et al. | |
| 6,461,353 B1 | 10/2002 | Baker, Jr. et al. | |

(56) References Cited

U.S. PATENT DOCUMENTS

| | | |
|---|---|---|
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,478,793 B1 | 11/2002 | Cosman et al. |
| 6,482,204 B1 | 11/2002 | Lax et al. |
| 6,491,690 B1 | 12/2002 | Goble et al. |
| 6,494,880 B1 | 12/2002 | Swanson et al. |
| 6,500,172 B1 | 12/2002 | Panescu et al. |
| 6,500,173 B2 | 12/2002 | Underwood et al. |
| 6,506,189 B1 | 1/2003 | Rittman, III et al. |
| 6,517,568 B1 | 2/2003 | Sharkey et al. |
| 6,530,992 B1 | 3/2003 | Yang et al. |
| 6,533,780 B1 | 3/2003 | Laird et al. |
| 6,540,741 B1 | 4/2003 | Underwood et al. |
| 6,544,195 B2 | 4/2003 | Wilson et al. |
| 6,547,810 B1 | 4/2003 | Sharkey et al. |
| 6,557,559 B1 | 5/2003 | Eggers et al. |
| 6,558,381 B2 | 5/2003 | Ingle et al. |
| 6,575,968 B1 | 6/2003 | Eggers et al. |
| 6,575,969 B1 | 6/2003 | Rittman, III et al. |
| 6,584,360 B2 | 6/2003 | Francischelli et al. |
| 6,587,731 B1 | 7/2003 | Ingle et al. |
| 6,602,248 B1 | 8/2003 | Sharps et al. |
| 6,604,003 B2 | 8/2003 | Fredricks et al. |
| 6,613,047 B2 | 9/2003 | Edwards |
| 6,620,155 B2 | 9/2003 | Underwood et al. |
| 6,645,203 B2 | 11/2003 | Sharkey et al. |
| 6,645,464 B1 | 11/2003 | Hainfield |
| 6,652,513 B2 | 11/2003 | Panescu et al. |
| 6,673,023 B2 | 1/2004 | Pfluegger |
| 6,673,063 B2 | 1/2004 | Brett |
| 6,702,810 B2 | 3/2004 | McClurken et al. |
| 6,706,038 B2 | 3/2004 | Francischelli et al. |
| 6,712,811 B2 | 3/2004 | Underwood et al. |
| 6,712,813 B2 | 3/2004 | Ellman et al. |
| 6,712,816 B2 | 3/2004 | Hung et al. |
| 6,723,091 B2 | 4/2004 | Goble et al. |
| 6,726,684 B1 | 4/2004 | Woloszko et al. |
| 6,726,685 B2 | 4/2004 | To et al. |
| 6,730,081 B1 | 5/2004 | Desai |
| 6,733,496 B2 | 5/2004 | Sharkey et al. |
| 6,736,815 B2 | 5/2004 | Ginn |
| 6,749,605 B2 | 6/2004 | Ashley et al. |
| 6,749,617 B1 | 6/2004 | Palasis et al. |
| 6,767,347 B2 | 7/2004 | Sharkey et al. |
| 6,772,012 B2 | 8/2004 | Ricart et al. |
| 6,783,532 B2 | 8/2004 | Steiner et al. |
| 6,796,982 B2 | 9/2004 | Carmel et al. |
| 6,821,276 B2 | 11/2004 | Lambrecht et al. |
| 6,827,716 B2 | 12/2004 | Ryan et al. |
| 6,832,996 B2 | 12/2004 | Woloszko et al. |
| 6,832,997 B2 | 12/2004 | Uchida et al. |
| 6,837,884 B2 | 1/2005 | Woloszko |
| 6,837,888 B2 | 1/2005 | Ciarrocca et al. |
| 6,846,314 B2 | 1/2005 | Shapira |
| 6,878,155 B2 | 4/2005 | Sharkey et al. |
| 6,896,675 B2 | 5/2005 | Leung et al. |
| 6,929,640 B1 | 8/2005 | Underwood et al. |
| 6,997,941 B2 | 2/2006 | Sharkey et al. |
| 7,097,641 B1 | 8/2006 | Arless et al. |
| 7,267,683 B2 | 9/2007 | Sharkey et al. |
| 7,282,061 B2 | 10/2007 | Sharkey et al. |
| 7,309,336 B2 | 12/2007 | Ashley et al. |
| 7,400,930 B2 | 7/2008 | Sharkey et al. |
| 7,593,778 B2 | 9/2009 | Chandran et al. |
| 2001/0001314 A1 | 5/2001 | Davison et al. |
| 2001/0025176 A1 | 9/2001 | Ellsberry et al. |
| 2001/0025177 A1 | 9/2001 | Eoloszko et al. |
| 2001/0032002 A1 | 10/2001 | McClurken et al. |
| 2002/0032441 A1 | 3/2002 | Ingle et al. |
| 2002/0072688 A1 | 6/2002 | Burbank et al. |
| 2002/0128641 A1 | 9/2002 | Underwood et al. |
| 2002/0138020 A1 | 9/2002 | Pflueger |
| 2002/0138091 A1 | 9/2002 | Pflueger |
| 2002/0188290 A1 | 12/2002 | Sharkey et al. |
| 2002/0188292 A1 | 12/2002 | Sharkey et al. |
| 2002/0193790 A1 | 12/2002 | Fleischman et al. |
| 2003/0158545 A1 | 8/2003 | Hovda et al. |
| 2004/0002746 A1 | 1/2004 | Ryan et al. |
| 2004/0059254 A1 | 3/2004 | Pflueger |
| 2004/0064137 A1 | 4/2004 | Pellegrino et al. |
| 2004/0176759 A1 | 9/2004 | Krishnamurthy et al. |
| 2004/0193151 A1 | 9/2004 | To et al. |
| 2004/0215181 A1 | 10/2004 | Christopherson et al. |
| 2005/0177209 A1 | 8/2005 | Leung et al. |
| 2005/0209530 A1 | 9/2005 | Pflueger |
| 2005/0234445 A1 | 10/2005 | Conquergood et al. |

FOREIGN PATENT DOCUMENTS

| | | |
|---|---|---|
| EP | 1059067 | 12/2000 |
| EP | 1402838 | 9/2003 |
| IT | 1246197 | 11/1994 |
| WO | WO 98/17190 | 4/1998 |
| WO | WO 99/47058 | 9/1999 |
| WO | WO 01/45579 | 6/2001 |
| WO | WO 01/57655 | 8/2001 |
| WO | WO 01/62168 | 8/2001 |
| WO | WO 01/74251 | 10/2001 |
| WO | WO 03/073948 | 9/2003 |
| WO | WO 2005/110263 | 11/2005 |

OTHER PUBLICATIONS

Case et al., "Changes of Intradisc Pressure Versus Volume Change", J. Clin. Laser Med & Surg., Jun. 1995, vol. 13(3), pp. 143-147.

Choy et al., "B. Fall of Intradiscal Pressure with Laser Ablation", J. Clin. Laser Med & Surg., vol. 13, No. 3, 1995, pp. 149-151.

Cripton et al., "A Minimally Disruptive Technique for Measuring Intervertebral Disc Pressure in Vitro: Application to the Cervical Spine", J. Biomech, Apr. 2001, vol. 34 (4), 545-549.

Ferrante, Michael F., "Radiofrequency sacroiliac join denervation for sacroiliac syndrome", Regional Anesthesia and Pain Medicine; 2001; 26(2); pp. 137-142.

Freemont, "Nerve Ingrowth into Diseased Intervertebral Disc in Chronic Back Pain", The Lancet, 1997, 350, pp. 178-181.

Houpt, "Experimental Study of Temperature Distributions and Thermal Transport During Radio Frequency Current Therapy of the Intervertebral Disc", Spine, 1996 21(15), 1808-1813.

McNally et al., "Development and Validation of a New Transducer for Intradiscal Pressure Measurement", J. Biomed. Eng., Nov. 1992, vol. 14(6) 495-498.

Panjabi et al., "Intrinsic Disc Pressure as a Measurement of Integrity of the Lumbar Spine", Spine, Aug. 1988, vol. 13(8) 913-977.

Wilke et al., "New in Vivo Measurements of Pressures in the Intervertebral Disc in Daily Life", Spine, Apr. 1999, vol. 15:24(8), 913-977.

\* cited by examiner

FIG.2A  FIG.2B  FIG.2C
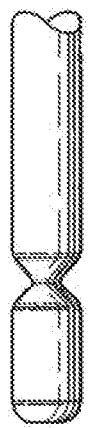
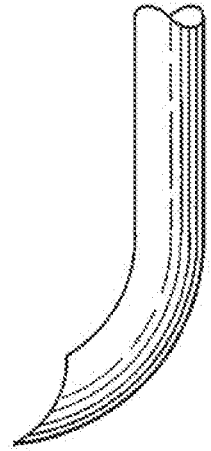
FIG.2D  FIG.2E  FIG.2F

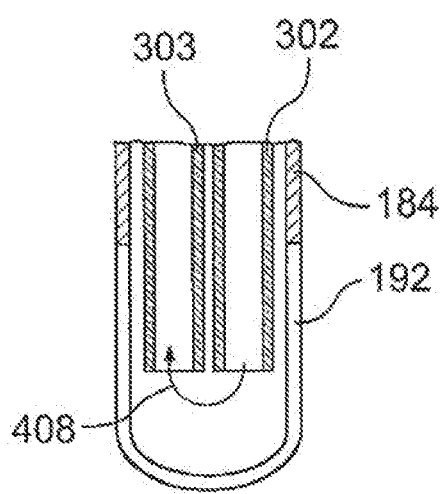 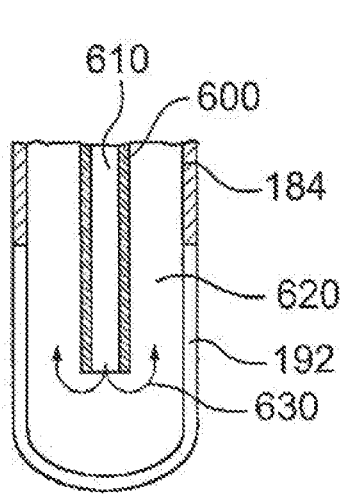 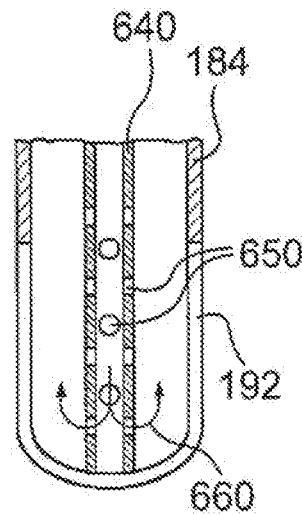
FIG.6A  FIG.6B  FIG.6C
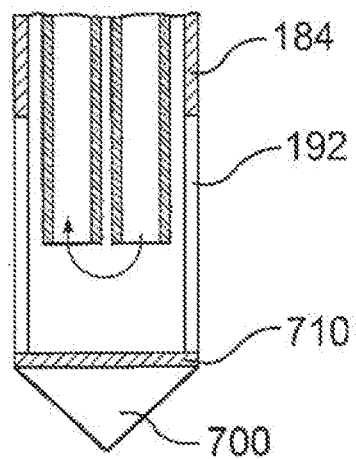
FIG.7

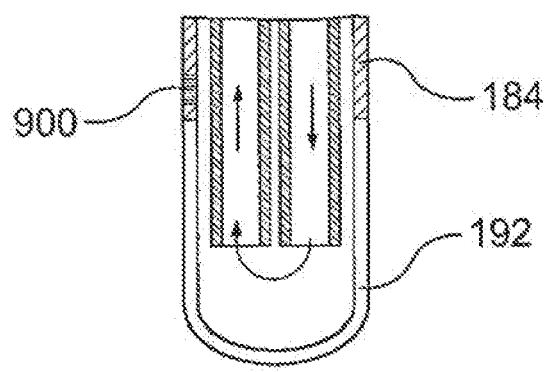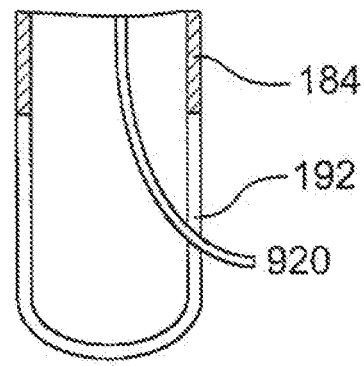
FIG.9A  FIG.9B
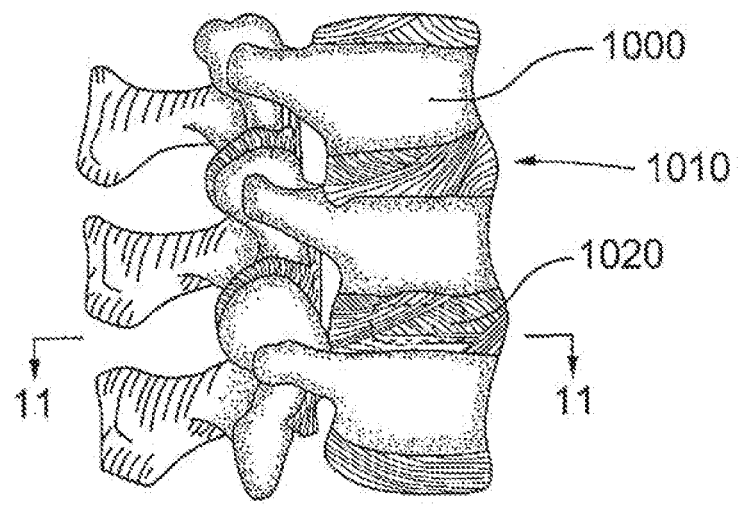
FIG.10 though the nucleus pulposus is gelatinous and somewhat fluid while the annulus fibrosus comprises circularly arranged fibers, the border between these components is not distinct in a healthy adult disc. Any distinction is less apparent in a damaged disc where tissues are intermingled in a gradual transition layer.

ELECTROSURGICAL TISSUE TREATMENT DEVICE

CROSS-REFERENCE TO RELATED APPLICATION

This application is a continuation of U.S. application Ser. No. 14/145,429, filed Dec. 13, 2013, which is a division of U.S. application Ser. No. 13/964,460 filed on Aug. 12, 2013, now U.S. Pat. No. 8,740,897, which is a continuation of U.S. application Ser. No. 11/939,280, filed Nov. 13, 2007, now U.S. Pat. No. 8,518,036, which is a continuation of Ser. No. 11/105,524, filed Apr. 14, 2005, now U.S. Pat. No. 7,294,127, which is a continuation-in-part of U.S. application Ser. No. 10/087,856, filed Mar. 5, 2002, now U.S. Pat. No. 6,896,675 and claims the benefit of U.S. provisional application No. 60/604,348, filed Aug. 25, 2004.

TECHNICAL FIELD

The present invention relates to a medical device, system and method for applying energy, particularly radio frequency electrical energy, to a patient's body.

BACKGROUND OF THE ART

The human intervertebral junction is characterized principally by an intervertebral disc interposed between adjacent vertebral surfaces. The size and configuration of discs vary between the six discs of the cervical region, the twelve discs of the thoracic region, six of the lumbar region and one disc between the sacrum and coccyx.

Intervertebral discs are neither homogeneous nor static. Changes to a disc can affect the vertebral column activity significantly. The intervertebral disc is a complex structure where its dynamic properties result from the interaction of a central, gelatinous nucleus pulposus encircled by a tough, fibrous, semielastic annulus fibrosus. Further, thin cartilage endplates and vertebral body ring apophyseal attachments of the annulus fibrosus join the disc to the vertebrae craniad and caudad to the disc. Although the nucleus pulposus is gelatinous and somewhat fluid while the annulus fibrosus comprises circularly arranged fibers, the border between these components is not distinct in a healthy adult disc. Any distinction is less apparent in a damaged disc where tissues are intermingled in a gradual transition layer.

The annulus fibrosus is composed of concentric layers of fibrocartilage, in which collagen fibers are arranged in parallel strands running obliquely between vertebral bodies. The inclination is reversed in alternate layers thereby crossing over each other obliquely. In children and adolescents, the nucleus pulposus is an amorphous colloidal mass of gelatinous material containing glycosaminoglycans, collagen fibrils, mineral salt, water and cellular elements. The nucleus pulposus has an important function in nutrition of the disc and contributes to the mechanical ability of the disc to act as a shock absorber and allow flexibility. The nucleus pulposus is normally under pressure and is contained within an ovoid cavity formed laterally by the annulus fibrosus and bounded by thin plates of hyaline cartilage endplates covering the adjacent vertebrae.

The intervertebral discs form about one-quarter the length of the vertebral column in a healthy adult human. Discs are thickest in the cervical and lumbar regions, where the movements of the vertebral column are greatest. The vertebral column, including the intervertebral discs, undergo various morphological and biochemical changes over time, such as dehydration of the discs and concaving vertebral bodies. As a result, the size and configuration of the disc components vary considerably from person to person.

Lower back injuries and chronic back pain are a major health problem resulting not only in a debilitating condition for the patient, but also in the consumption of a large proportion of funds allocated for health care, social assistance and disability programs. Disc abnormalities and pain may result from trauma, repetitive use in the workplace, metabolic disorders, inherited proclivity or aging. The existence of adjacent nerve structures and innervation of the disc are very important issues in respect to patient treatment for back pain.

Common disorders of the intervertebral disc include localized tears or fissures in the annulus fibrosus; disc herniations with contained or escaped extrusions of the nucleus pulposus; and chronic circumferential bulging of discs. For most patients, however, a well-defined abnormality cannot be found to solely explain the cause of the low back pain, making treatment and pain management very difficult. Since isolating a specific anatomic disorder as the sole cause of pain is rare, most patients are merely treated symptomatically to reduce pain, rather than receiving treatment to eliminate the cause of the condition.

One course of pain may be attributed to the structure of the annulus fibrosus. The annulus fibrosus is thinner nearer to the posterior than to the anterior margin of the disc, and many disc ruptures occur in the posterior region thereby exerting pressure on the adjacent nerve fibers causing pain. The pain experienced by the disc exerting pressure on the adjacent nerves is characterized by referred pain, or pain felt predominantly elsewhere in the body where the affected nerve travels. A common example of this is sciatica where an intervertebral disc exerts pressure on the sciatic nerve.

Another cause of pain resulting from disc pathology is chemically-induced pain. The nucleus pulposus contains chemicals that may induce pain if contact is made with certain nerve structures. If an intervertebral disc is herniated severely enough that a portion of the nucleus pulposus is extruded from the disc, and the portion comes in contact with an adjacent nerve, chemically-induced pain can be felt. This is also a cause of sciatica.

Increasingly, evidence suggests that the source of back pain in many patients is a result of nerves within the degenerated disc itself or nerves that have grown into the disc in concordance with disc injury. For example, as documented by Jonathan C. Houpt, B A, Edison S. Conner, M D, and Eric W. McFarland in "Experimental Study of Temperature Distributions and Thermal Transport During Radio frequency Current Therapy of the Intervertebral Disc", Spine. 1996; 21(15), 1808-1813, afferent innervation of the outer half of the annulus fibrosus has been established whereas the nucleus pulposus contains no nerves or blood vessels. Pain response has been widely reported in response to specific stimulation of the outer layers of the annulus fibrosus. In another study documented by A. J. Freemont, "Nerve ingrowth into diseased intervertebral disc in chronic back pain", The Lancet. 1997; 350, 178-181, nociceptive nerves were found ingrown deeper into the disc, as far as the nucleus pulposus, in association with disc degeneration. The pain experienced from nerves in a damaged intervertebral disc is more localized to the spine. The stimulation can be both mechanical and chemical. Some patients may feel a combination of back pain and referred pain indicating that pain is being transmitted both from nerves in the disc and from impinged nerves adjacent to the disc. It appears that the disc is devoid of temperature-sensing neurological structures, possibly due to the fact that the disc is at core body temperature, and only mechanical and chemical stimulus-sensing nociceptors exist in the disc.

Where patients are diagnosed with clear chronic discogenic pain (i.e. pain originating from a disc), complete surgical removal of the intervertebral disc (called discectomy) and fusion of the adjacent vertebrae is often carried out with success rates over 80% in measurable pain reduction after surgery. Such major surgical procedures are highly invasive, expensive and involve significant risk. Furthermore motion is impeded once the vertebrae are fused and there may be adverse mechanical effects on the adjacent remaining discs.

To alleviate some of the disadvantages of open-surgery discectomy, percutaneous methods of removing the disc or part of the disc have been practiced. Methods that remove part of the nucleus pulposus are designed to decrease the volume in order to reduce internal disc pressure thus reducing external pressure exerted on adjacent nerves. Examples of such methods that include mechanical means can be found in, for example, U.S. Pat. No. 4,369,788 to Goald that describes the use of a mechanical device for use in microlumbar discectomy, and in U.S. Pat. No. 5,201,729 to Hertzmann et al. that describes a percutaneous method of discectomy using a laser. Other methods of removing the disc or part of the disc include chemically dissolving the nucleus pulposus using the enzyme Chymopapain. U.S. Pat. No. 6,264,650 to Hovda et al. describes a method of vaporizing a portion of the nucleus pulposus using radio frequency electrical current. These prior art methods have shown variable success and there are several advantages of percutaneous procedures over open surgical discectomy and vertebral fusion including less trauma to the patient, preserved spinal movement, less disruptive effect on adjacent discs, less risk of infection and less risk of accidental injury. However, these methods involve removing a portion of the nucleus pulposus, which is essential to the maintenance of the disc. Further, the damaged annulus fibrosus is not treated.

Due to the pain reduction success of surgical discectomy, less drastic means of denervating rather than surgically removing the disc are of significant interest. To denervate is to intervene with the transmission of a sensory signal in a nerve. A denervated disc does not cause discogenic pain and the disc is left intact to preserve its mechanical function. Denervating the disc especially by using percutaneous probes is much less invasive, less costly and less risky. The procedure is also simpler to administer and does not require the fusing of adjacent vertebrae thereby better preserving the patient's freedom of movement.

A minimally invasive technique of delivering high-frequency electrical current has been shown to relieve localized pain in many patients. Generally, the high-frequency current used for such procedures is in the radio frequency (RF) range, i.e. between 100 kHz and 1 GHz and more specifically between 300-600 kHz. The RF electrical current is typically delivered from a generator via connected electrodes that are placed in a patient's body, in a region of tissue that contains a neural structure suspected of transmitting pain signals to the brain. The electrodes generally include an insulated shaft with an exposed conductive tip to deliver the radio frequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations. This procedure may be done in a monopolar mode where a second dispersive electrode with a large surface area is placed on the surface of a patient's body to complete the circuit, or in a bipolar mode where a second radio frequency electrode is placed at the treatment site. In a bipolar procedure, the current is preferentially concentrated between the two electrodes.

In order to extend the size of a lesion, radio frequency treatment may be applied in conjunction with a cooling mechanism, whereby a cooling means is used to reduce the temperature of the tissue in the vicinity of an energy delivery device, allowing a higher voltage to be applied without causing an unwanted increase in local tissue temperature. The application of a higher voltage allows regions of tissue further away from the energy delivery device to reach a temperature at which a lesion can form, thus increasing the size/volume of the lesion.

U.S. Pat. No. 6,379,348, issued on Apr. 30, 2002 to Onik, describes a combined electrosurgical-cryosurgical instrument for tissue ablation. The instrument and method of use described therein does not utilize a cooling fluid to allow a higher radio frequency voltage to be applied, but rather utilizes a cryogenic coolant to generate a lesion, i.e. the cooling itself causes a change in tissue characteristics. U.S. Pat. No. 5,603,221, issued on Feb. 18, 1997 to Maytal, describes a system including a plurality of cryogenic probes. Maytal's probes use cryogenic gases to cool a body tissue sufficiently to form a lesion within the body tissue.

The treatment of pain using high-frequency electrical current has been applied successfully to various regions of patients' bodies suspected of contributing to chronic pain sensations. For example, with respect to back pain, which affects millions of individuals every year, high-frequency electrical treatment has been applied to several tissues, including intervertebral discs, facet joints, sacroiliac joints as well as the vertebrae themselves (in a process known as intraosseous denervation). In addition to creating lesions in neural structures, application of RF energy has also been used to treat tumors throughout the body.

In an effort to reduce back pain through early intervention techniques, some investigators have focused upon nerves contained within the vertebral bodies which are adjacent to the intervertebral discs. For example, in PCT Patent Publication No. WO 01/0157655, Heggeness discloses ablating nerves contained within the vertebral body (intraosseous nerves) by first boring into the vertebral body with a nerve ablation device, placing the tip of the device in close proximity to the nerve, and then ablating the nerve using the tip. However, previous techniques fail to describe how to effectively carry out nerve ablation when the precise location of the intraosseous nerve is unknown, or when the electrode tip cannot be maneuvered relatively close to the intraosseous nerve.

With respect to the intervertebral disc itself, U.S. Pat. No. 5,433,739 to Sluijter et al. describes a method of relieving back pain through percutaneous insertion of a needle or electrode into the center of the intervertebral disc within the nucleus pulposus under fluoroscopy or other imaging control. The U.S. Pat. No. 5,433,739 patent describes the heating of the outer layers of the annulus fibrosus to a temperature that is lethal to the nerve structures thereby denervating the disc to relieve discogenic pain. The temperature of the tissue is increased by applying high frequency electric current through the tissue.

It is well known to those skilled in the art that percutaneous access to an intervertebral lumbar disc involves either a posterolateral approach or an anterior approach. The anterior approach is more invasive than the posterolateral approach because of the organs in the abdominal and pelvic cavities. The most common percutaneous approach to the lumbar disc, to those skilled in the art, is to insert a needle or tube posterolateral to the disc, just lateral of the zygapophyseal joint, inferior to the spinal nerve and into the posterolateral region of the annulus fibrosus.

In accordance with U.S. Pat. Nos. 5,980,504; 6,007,570; 6,073,051; 6,095,149; 6,099,514; 6,122,549; 6,126,682; 6,258,086 B1; 6,261,311 B1; 6,283,960 B1; and 6,290,715 B1 ("the Sharkey et al. patents") to Sharkey et al. to permit percutaneous access to the posterior half of the nucleus or to the posterior inner wall of the disc, a flexible heating element may be inserted into the nucleus pulposus through a hollow tube that has been inserted through the annulus fibrosus. The flexible heating element has sufficient rigidity to be advanced longitudinally under force through the nucleus pulposus while having sufficient flexibility to be compliant to the inner wall of the annulus fibrosus. The heating element is guided by sliding contact with the inner wall and ideally should not puncture or damage the annulus fibrosus during positioning. Another embodiment disclosed in U.S. Pat. No. 6,258,086 B1 is a flexible probe that contains an activation element on the distal portion that changes the shape of the probe once it is in the nucleus pulposus. According to the Sharkey et al. patents, the flexible heating elements operate to denervate the outer layers of the annulus fibrosus as well as modulate the collagen in the annulus fibrosus by applying heat. Raising the temperature above about 60° C. will break structural bonds of collagen fibers causing them to contract and tighten. This collagen-tightening effect is lost once the temperature of the collagen is raised above about 75° C., where the fibers loosen, resulting in zero net volume change.

There is interest among researchers that the application of high frequency current without a rise in temperature alters nerve function to relieve pain. Use of high frequency current without heating to relieve pain by modifying neural tissue is described in U.S. Pat. Nos. 5,983,141; 6,161,048; 6,246,912; and 6,259,952 ("the Sluijter et al. patents") to Sluijter et al. These patents describe the use of a modified signal wave that includes rest periods to allow heat to dissipate. The modified high frequency signal is applied to the patient using a single active electrode and a ground electrode attached to the skin of the patient. These disclosures (the Sluijter et al. patents) do not discuss using high frequency current to increase collagen production nor do they discuss this application in the intervertebral disc. The disclosures that are specifically designed for treatment of intervertebral discs (the Sharkey et al. patents; U.S. Pat. No. 5,433,739 of Sluijter et al.; and Finch PCT publication number WO 01/45579) do not discuss the application of high frequency current without a rise in temperature to alter nerve function to relieve pain or to cause collagen production to increase. The advantages of non-thermal application of high frequency electrical current to treat intervertebral discs include reduced risk of thermal damage, increased production of collagen to strengthen the annulus fibrosus, and reduced discogenic pain while stimulating the healing processes.

The above referenced publications describe the use of monopolar devices for treatment procedures and are therefore restricted by the limitations of using a monopolar probe. For example, since energy is primarily concentrated around the lone electrode in a monopolar device, precise knowledge of the location of the tissue to be treated is required. In contrast, in a bipolar procedure, the energy is concentrated between two electrodes allowing a tissue to be affected by the treatment procedure provided it is located substantially between the electrodes. The use of two electrodes in a bipolar configuration also allows for the creation of a more uniform lesion than with a single electrode where the energy is concentrated at the surface of the electrode.

Thus, it would be beneficial to have a device and a system that overcomes some or all of the limitations of the prior art.

SUMMARY OF THE INVENTION

There is a continued need for improvement in systems used for RF treatment of bodily tissue. Specifically, it would be beneficial to incorporate cooled probes and temperature and impedance monitoring concepts into an RF treatment system. In addition, the system should be capable of providing newer treatment modalities, such as bipolar RF. Finally, the probes used in the system should be relatively compact while still providing the benefits and advantages mentioned herein. Thus, the present invention attempts to overcome some or all of the deficiencies in the prior art.

In accordance with a first aspect of the present invention, a method of treating spinal tissue of a patient's body is provided. The method uses a system comprising an energy source and first and second internally-cooled probe assemblies, wherein each of the probe assemblies comprises an electrically conductive energy delivery device electrically coupled to the energy source, and the method optionally comprises the following steps: inserting the energy delivery devices of the first and second internally-cooled probe assemblies into spaced-apart treatment sites for the spinal tissue; delivering energy from the energy source to the spinal tissue through the energy delivery devices; delivering a cooling fluid to the energy delivery devices; and controlling the delivery of energy and the delivery of the cooling fluid to the energy delivery devices such that the lesion extends between the energy delivery devices.

The spinal tissue being treated may be selected from the group consisting of an intervertebral disc, spinal neural tissue and a vertebra or portions thereof. Furthermore, the energy source may be a radio-frequency generator and the step of delivering energy may comprise delivering electrical current in a radio-frequency range. Additionally, the energy delivery devices may be operated in a bipolar mode, whereby delivered energy is preferentially concentrated between the energy delivery devices.

As a feature of this aspect, the spinal tissue may comprise a vertebra and the lesion may be created in order to denervate a neural structure within the vertebra or in order to treat a tumor within the vertebra.

As a further feature of this aspect, the spinal tissue may comprise an intervertebral disc and the energy delivery device of one of the first and second probe assemblies may be placed within a nucleus pulposus of the intervertebral disc and the energy delivery device of the other of the first and second probe assemblies may be placed within an annulus fibrosus of the intervertebral disc. As an additional feature, the energy delivery devices of each of the first and second probe assemblies may be located partially within a nucleus pulposus of the intervertebral disc and partially within an annulus fibrosus of the intervertebral disc, such that at least an equal amount of energy is delivered to the nucleus pulposus as to the annulus fibrosus. As a further feature, the energy delivery device of one of the first and second probe assemblies may be placed within an anterior portion of the intervertebral disc and the energy delivery device of the other of the first and second probe assemblies may be placed within a posterior portion of the intervertebral disc.

As an additional feature of this aspect, the delivery of energy and the delivery of the cooling fluid may be controlled based on a distance between the energy delivery devices.

According to another aspect, a method is disclosed of treating spinal tissue of a patient's body using a system comprising an energy source and first and second internally-cooled probe assemblies, wherein each of the probe assemblies comprises an electrically conductive energy delivery device electrically coupled to the energy source. The method may include inserting the energy delivery devices of the first and second internally-cooled probe assemblies into spaced-apart treatment sites for the spinal tissue; delivering energy from the energy source to the spinal tissue through the energy delivery devices in a bipolar mode that concentrates delivered energy between the energy delivery devices to create a lesion within the spinal tissue; cooling the energy delivery devices; and controlling the delivery of energy to and the cooling of the energy delivery devices at least in part based on a distance between the energy delivery devices such that the lesion extends between the energy delivery devices.

According to another aspect, a method is disclosed of treating spinal tissue of a patient's body using a system comprising an energy source and first and second internally-cooled probe assemblies, wherein each of the probe assemblies comprises an electrically conductive energy delivery device electrically coupled to the energy source. The method may include inserting the energy delivery devices of the first and second internally-cooled probe assemblies into spaced-apart treatment sites for the spinal tissue; delivering energy from the energy source to the spinal tissue through the energy delivery devices in a bipolar mode that concentrates delivered energy between the energy delivery devices to create a lesion within the spinal tissue; cooling the energy delivery devices using at least one electrothermal device; and controlling the delivery of energy to and the cooling of the energy delivery devices such that the lesion extends between the energy delivery devices.

According to another aspect, a device for treating spinal tissue of a patient's body may include an energy source and first and second probe assemblies. Each of the probe assemblies may have an electrically conductive energy delivery device electrically coupled to the energy source, and may also have an electrothermal device for cooling the probe assembly. The device is configured so that the energy source delivers energy to the spinal tissue through the energy delivery devices in a bipolar mode that concentrates delivered energy between the energy delivery devices to create a lesion within the spinal tissue while the electrothermal devices cool the probe assemblies.

These features and others will become apparent in the detailed description that follows.

BRIEF DESCRIPTION OF THE DRAWINGS

In order that the invention may be readily understood, embodiments of the invention are illustrated by way of examples in the accompanying drawings, in which:

FIGS. 2A to 2F depict side views of alternate embodiments of a distal tip region of a probe assembly;

FIGS. 6A-6C are sectional views of various embodiments of a liquid-cooled distal tip region of a probe assembly;

FIG. 7 is a sectional view of an embodiment of a liquid-cooled distal tip region comprising an impedance monitoring tip;

FIGS. 9A and 9B are sectional views of alternate embodiments of a liquid-cooled distal tip region illustrating various embodiments of a temperature sensing element;

FIG. 10 is a lateral view of a portion of a human spine;

DETAILED DESCRIPTION OF THE INVENTION

Figure 1:
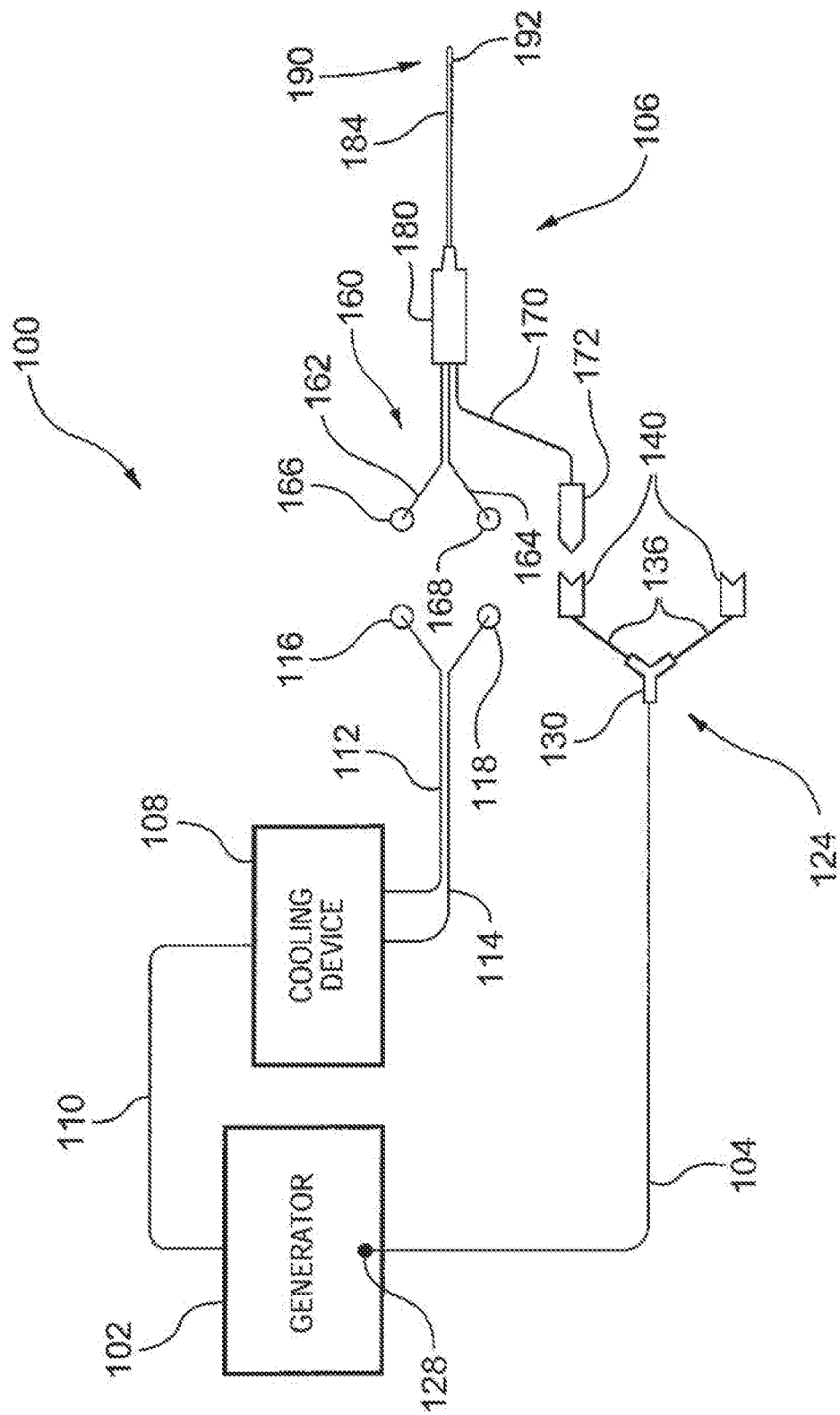
FIG. 1 is an illustration of a portion of a first embodiment of a system of the present invention.

With specific reference now to the drawings in detail, it is stressed that the particulars shown are by way of example and for purposes of illustrative discussion of some embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to any effect achieved through the application of energy to a tissue in a patient's body, and the invention is not intended to be limited in this regard. Furthermore, for the purposes of this description, proximal generally indicates that portion of a device or system next to or nearer to a user (when the device is in use), while the term distal generally indicates a portion further away from the user (when the device is in use).

With reference to FIG. 1, a first embodiment of a system 100 of the present invention is shown. System 100 comprises a generator 102, a cable 104, first and second probe assemblies 106 (only one probe assembly is shown), one or more cooling devices 108, a pump cable 110, one or more proximal cooling supply tubes 112 and one or more proximal cooling return tubes 114. In this embodiment, generator 102 is a radio frequency (RF) generator, but may optionally be any energy source that may deliver other forms of energy, including but not limited to microwave energy, thermal energy, ultrasound and optical energy. Generator 102 may comprise a display means incorporated into said generator. Said display means may be operable to display various aspects of a treatment procedure, including but not limited to any parameters that are relevant to a treatment procedure, such as temperature, impedance, etc. and errors or warnings related to a treatment procedure. If no display means is incorporated into generator 102, generator 102 may comprise a means of transmitting a signal to an external display. In the first embodiment, generator 102 is operable to communicate with one more devices, for example with one or more of first and second probe assemblies 106 and the one or more cooling devices 108. Such communication may be unidirectional or bidirectional depending on the devices used and the procedure performed. An example of an RF generator that fulfills the above criteria is the Pain Management Generator (PMG) of Baylis Medical Company Inc. (Montreal, QC, Canada).

As illustrated in FIG. 1, in this first embodiment of a system of the present invention, a distal region 124 of cable 104 comprises a splitter 130 that divides cable 104 into two distal ends 136 as illustrated in FIG. 1 such that two probe assemblies 106 can be connected to cable 104. A proximal end 128 of cable 104 is connected to generator 102. This connection can be permanent, whereby, for example, the proximal end 128 of cable 104 is embedded within generator 102, or temporary, whereby, for example, the proximal end 128 of cable 104 is connected to generator 102 via an electrical connector. The two distal ends 136 of cable 104 terminate in connectors 140 operable to couple to probe assemblies 106 and establish an electrical connection between probe assemblies 106 and generator 102. In alternate embodiments (not shown), system 100 may comprise a separate cable for each probe assembly 106 being used to couple probe assemblies 106 to generator 102. Alternatively, splitter 130 may comprise more than two distal ends. Such a connector would be useful in embodiments where it would be desirable to connect more than two devices to generator 102, for example, if more than two probe assemblies are being used or if separate temperature sensors (i.e. not attached to the probe assemblies) are to be placed in a patient's body.

One or more cooling devices 108 may comprise any means of reducing a temperature of material located at and proximate to one or more of probe assemblies 106. In the first embodiment, one or more cooling devices 108 comprises two peristaltic pumps operable to circulate a fluid from the one or more cooling devices 108 through one or more proximal cooling supply tubes 112, probe assemblies 106, one or more proximal cooling return tubes 114 and back to the one or more cooling devices 108. The fluid may be water or any other suitable fluid. In alternate embodiments, one or more cooling devices 108 may comprise only one peristaltic pump or one or more electrothermal cooling devices or any other cooling means.

In the first embodiment, system 100 comprises a means of facilitating communication between the one or more cooling devices 108 and generator 102, and one or more cooling devices 108 is operable to communicate at least uni-directionally and optionally bi-directionally, with generator 102. In this way, feedback control is established between the one or more cooling devices 108 and the generator 102. The feedback control of the first embodiment of the present invention involves generator 102, first and second probe assemblies 106 and the one or more cooling devices 108, although any feedback between any two devices is within the scope of the present invention. The feedback control may be implemented, for example, in a controller or control module which may be a component of generator 102. In this embodiment, generator 102 is operable to communicate bi-directionally with first and second probe assemblies 106 as well as with the one or more cooling devices 108. In the context of this invention, bi-directional communication refers to the capability of a device to both receive a signal from and send a signal to another device.

As an example of feedback control in system 100 of the present invention, generator 102 may receive temperature measurements from one or both of first and second probe assemblies 106. Based on the temperature measurements, generator 102 may perform some action, such as modulating the power that is sent to first and/or second probe assemblies 106. Thus, both probe assemblies 106 may be individually controlled based on their respective temperature measurements. For example, power to each of the probe assemblies could be increased when a temperature measurement is low or decreased when a measurement is high. This variation of power may be different for each probe assembly. In some cases, generator 102 may terminate power to one or more probe assemblies 106. Thus, generator 102 may receive a signal (e.g. temperature measurement) from one or both of first and second probe assemblies 106, determine the appropriate action, and send a signal (e.g. decreased or increased power) back to one or both of first and second probe assemblies 106. Alternatively, generator 102 may send a signal to the one or more cooling devices 108 to either increase or decrease the flow rate or degree of cooling being supplied to one or both of first and second probe assemblies 106.

Alternatively, if one or more cooling devices 108 comprises one or more peristaltic pumps, the one or more pumps may communicate a fluid flow rate to generator 102 and may receive communications from generator 102 instructing the pumps to modulate this flow rate. In some instances, the one or more peristaltic pumps may respond to generator 102 by changing the flow rate or turning off for a period of time. With cooling devices 108 turned off, any temperature sensing elements associated with probe assemblies 106 would not be affected by the cooling fluid allowing a more precise determination of the surrounding tissue temperature to be made. In addition, when using more than one probe assembly 106, the average temperature or a maximum temperature in the temperature sensing elements associated with probe assemblies 106 may be used to modulate cooling.

In other embodiments, the one or more cooling devices 108 may reduce the rate of cooling or disengage depending on the distance between the probe assemblies 106. For example, when the distance is small enough such that a sufficient current density exists in the region to achieve a desired temperature, little or no cooling may be required. In such an embodiment, energy is preferentially concentrated between first and second energy delivery devices 192 through a region of tissue to be treated, thereby creating a strip lesion. A strip lesion is characterized by an oblong volume of heated tissue that is formed when an active electrode is in close proximity to a return electrode of similar dimensions. This occurs because at a given power, the current density is preferentially concentrated between the electrodes and a rise in temperature results from current density.

One or more cooling devices 108 may also communicate with generator 102 in order to alert generator 102 to one or more possible errors and/or anomalies associated with one or more cooling devices 108. For example, if cooling flow is impeded or if a lid of the one or more cooling devices 108 is opened. Generator 102 may then act on the error signal by at least one of alerting a user, aborting the procedure, and modifying an action.

In still other embodiments, generator 102 may communicate with only one of the one or more cooling devices 108 or communication between devices may be unidirectional. For example, the one or more cooling devices 108 may be operable to receive incoming signals from generator 102 but not to send signals back to generator 102. In addition to the aforementioned feedback systems, generator 102 may respond to Somatosensory evoked potentials (SSEP)/Electromyogram (EMG) measurements or some other measure of patient response to a treatment procedure. Many variations in feedback control may exist in a system of the present invention, and the invention is not limited in this regard.

As illustrated in FIG. 1, the means of facilitating communication between the one or more cooling devices 108 and generator 102 may take the form of a pump cable 110 electrically connecting generator 102 to the one or more cooling devices 108. In other embodiments, generator 102 and the one or more cooling devices 108 may be connected with an RS-232 cable, a fiber optic cable, a USB cable, a Firewire™ (ieee 1394) cable or other means of electrical coupling. In yet further embodiments, communication between generator 102 and the one or more cooling devices 108 may be achieved using some other communication protocol including but not limited to infrared, wireless, Bluetooth™ and others and the invention is not limited in this regard.

In the first embodiment of a system of the invention as illustrated in FIG. 1, the one or more proximal cooling supply tubes 112 comprise proximal supply tube connectors 116 at the distal ends of the one or more proximal cooling supply tubes 112. Additionally, the one or more proximal cooling return tubes 114 comprise proximal return tube connectors 118 at the distal ends of the one or more proximal cooling return tubes 114. In the first embodiment, proximal supply tube connectors 116 are female luer-lock type connectors and proximal return tube connectors 118 are male luer-lock type connectors although other connector types are intended to be within the scope of the present invention.

In the first embodiment of a system of the present invention and referring still to FIG. 1, probe assembly 106 comprises a proximal region 160, a handle 180, a hollow elongate shaft 184 and a distal tip region 190 comprising one or more energy delivery devices 192. Proximal region 160 comprises distal cooling supply tube 162, distal supply tube connector 166, distal cooling return tube 164, distal return tube connector 168, probe assembly cable 170 and probe cable connector 172. In this embodiment, distal cooling supply tube 162 and distal cooling return tube 164 are flexible to allow for greater maneuverability of probe assemblies 106, but alternate embodiments with rigid tubes are possible.

In a first embodiment, distal supply tube connector 166 is a male luer-lock type connector and distal return tube connector 168 is a female luer-lock type connector. Thus, proximal supply tube connector 116 is operable to interlock with distal supply tube connector 166 and proximal return tube connector 118 is operable to interlock with distal return tube connector 168. This helps to establish a circuit within which a cooling fluid may flow while maintaining modularity of probe assembly 106. As a further benefit, having different types of connectors on either proximal tube as well as different types of connectors on either distal tube adds a measure of safety by ensuring that the tubes will not be connected incorrectly (i.e. supply to return and vice versa).

In the first embodiment illustrated in FIG. 1, probe cable connector 172 is located at a proximal end of probe assembly cable 170 and is operable to reversibly couple to one of connectors 140, thus establishing an electrical connection between generator 102 and probe assembly 106. Probe assembly cable 170 comprises one or more conductors depending on the specific configuration of probe assembly 106. For example, in this embodiment of system 100 of the present invention, probe assembly cable 170 comprises five conductors allowing probe assembly cable 170 to transmit RF current from generator 102 to the one or more energy delivery devices 192 as well as to connect multiple temperature sensing devices to generator 102 as discussed below.

One or more energy delivery devices 192 may comprise any means of delivering energy to a region of tissue adjacent distal tip region 190. For example, the one or more energy delivery devices 192 may comprise an ultrasonic device, an electrode or any other energy delivery means and the invention is not limited in this regard. Similarly, energy delivered via the one or more energy delivery devices 192 may take several forms including but not limited to thermal energy, ultrasonic energy, radio frequency energy, microwave energy or any other form of energy. In a first embodiment, the one or more energy delivery devices 192 comprise an electrode. The active region of the electrode may be 2-20 mm in length and energy delivered by the electrode is electrical energy in the form of current in the RF range. The size of the active region of the electrode in this embodiment is optimized for placement within an intervertebral disc, however, different sizes of active regions, all of which are within the scope of the present invention, may be used depending on the specific procedure being performed. In some embodiments, feedback from generator 102 may automatically adjust the exposed area of energy delivery device 192 in response to a given measurement such as impedance or temperature. This may be accomplished through the use of an adjustable insulation sleeve associated with energy delivery device 192. Adjustment of the insulation sleeve could be accomplished through sliding the sleeve proximally or distally along the energy delivery device. The adjustment may be done manually in other embodiments. Alternatively, additional conductive regions may be provided along distal tip region 190 proximate the energy delivery device 192. In such an embodiment, the size or shape of a lesion may be altered by selectively delivering energy through one or more of the additional conductive regions and energy delivery device 192. Furthermore, one or more energy delivery devices 192 may comprise any combination of active electrodes and return electrodes, as is well known in the art.

FIGS. 2A-2F show different shapes which the distal end of energy delivery device 192 can adopt for insertion in the patient's body. FIG. 2A shows a pencil tip. FIG. 2B shows a sharp beveled tip. FIG. 2C shows a blunt end when cutting or piercing is not required. FIGS. 2D and 2E show front and side views of a spatula shaped tip whereas FIG. 2F shows a curved tip with a cutting bevel end. The different shapes can allow for the current to be directed into the disc in a profile corresponding to the shape of the tip, thereby controlling the current density which will in turn control the size and shape of a lesion created in the tissue. These embodiments are intended to be exemplary only and various tip shapes may be used with the invention.

Figure 3A:
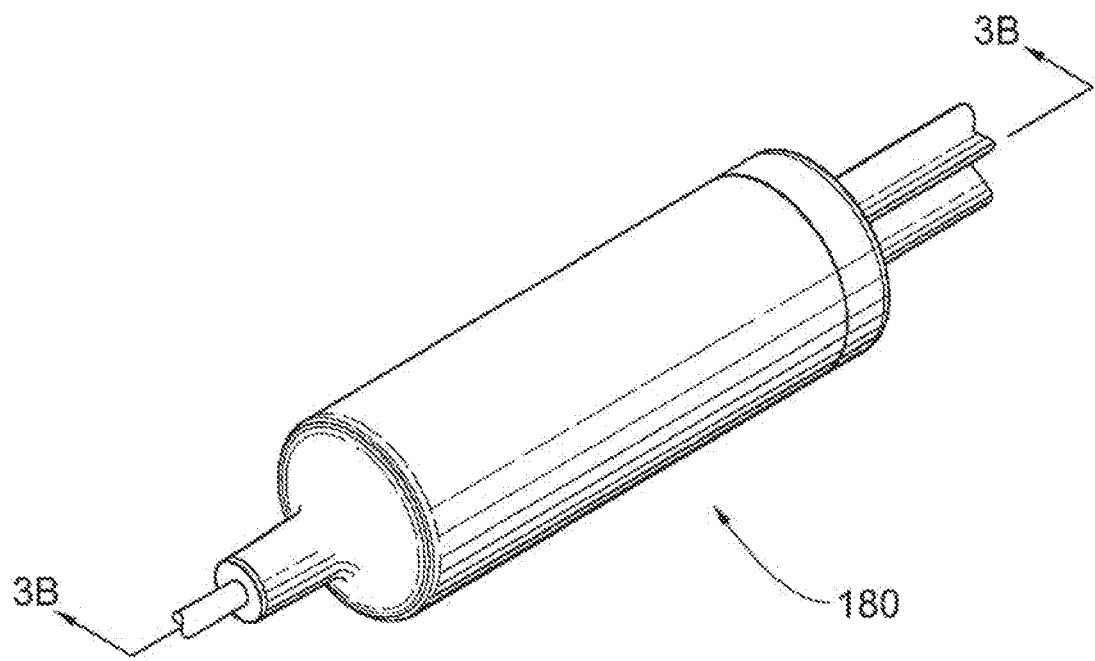
FIG. 3A is an isometric view of one embodiment of the handle of the probe assembly of the present invention.
Figure 3B:
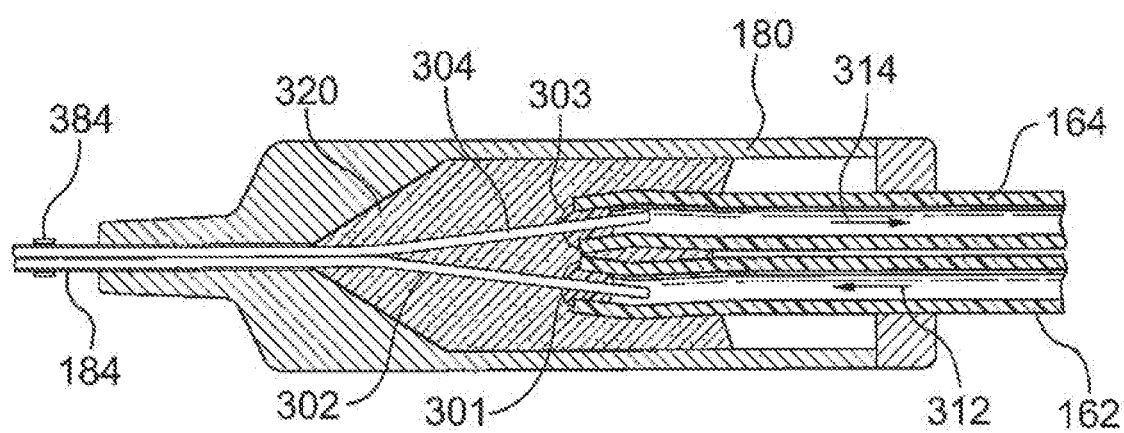
FIG. 3B is a longitudinal cross-section of one embodiment of a handle of the probe assembly of the present invention.
Figure 4:
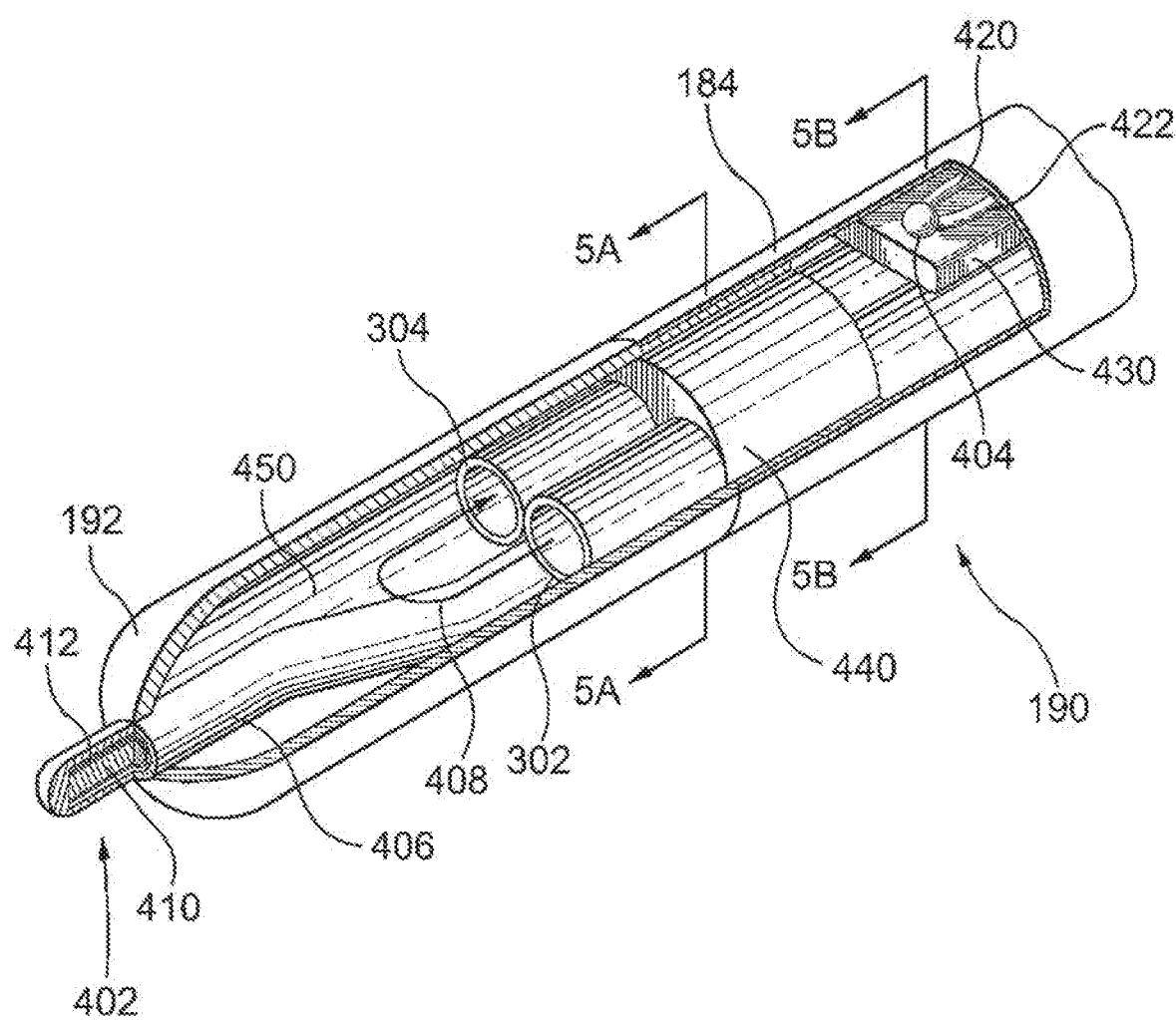
FIG. 4 is a perspective cut-away view of one embodiment of a distal tip region of a probe assembly of the present invention.

Cooling can be supplied to the one or more energy delivery devices 192 in various ways. The scope of the present invention includes any and all cooling means known in the art that may be used to provide cooling to the one or more energy delivery devices 192 and is not limited in this regard. In a first embodiment as has been described earlier, and with reference now to FIG. 3, distal cooling supply tube 162 and distal cooling return tube 164 are connected to shaft supply tube 302 and shaft return tube 304, respectively, within handle 180, using connecting means 301 and 303. Connecting means 301 and 303 can be any means of connecting two tubes including but not limited to ultraviolet (UV) glue, epoxy or any other adhesive as well as friction or compression fitting. Arrows 312 and 314 indicate the direction of flow of a cooling fluid supplied by the one or more cooling devices 108, in such embodiments that comprise a cooling fluid as part of the cooling means. In this first embodiment, shaft supply tube 302 and shaft return tube 304 are hypotubes made of a conductive material such as stainless steel. The hypotubes extend from handle 180 through a lumen of hollow elongate shaft 184 to distal tip region 190, as shown in FIG. 4, wherein arrow 408 indicates the direction of cooling fluid flow within a lumen 450 defined by the one or more energy delivery devices 192. Thus, using the configuration described in a first embodiment of a system of the invention, a cooling fluid is circulated between the one or more cooling devices 108 and distal tip region 190 of at least one probe assembly 106. As detailed later in the description, in alternate embodiments one hypotube may be used to supply cooling fluid to the one or more energy delivery devices 192 while two or more hypotubes may be used to return cooling fluid to the one or more cooling devices 108. The number of hypotubes used for supplying cooling fluid and the number used for returning cooling fluid and the combination thereof may vary and all such combinations are intended to be within the scope of the present invention.

In alternate embodiments of a system of the present invention, not all probe assemblies may be cooled, in which case, the probe assemblies that are not being cooled may not be associated with cooling tubes and the elongate hollow shafts of those probe assemblies may not comprise tubes for supplying cooling to and returning cooling from the distal tip regions of those probe assemblies.

In this first embodiment of a system of the present invention, distal cooling supply tube 162 may be connected to distal cooling return tube 164 in order to keep the tubing used in a system of the invention as organized as possible. This connection may be temporary, such as with a cable tie or other temporary connecting means, or may be more permanent, for example by using some form of adhesive bonding. Whether temporary or more permanent, this connection can be achieved using various means of connecting two or more tubes and the present invention is not limited in this regard. Referring again to FIG. 3, handle 180 may be at least partially filled with a filling agent 320 in order to lend more strength and stability to handle 180 as well as to hold the various cables, tubes and wires in place. Filling agent 320 may be epoxy or any other suitable material. In addition, handle 180 is operable to easily and securely couple to an optional introducer tube (discussed below) in a first embodiment where an introducer tube would facilitate insertion of the one or more probe assemblies 106 into a patient's body. For example, as shown in FIG. 3, handle 180 may taper at its distal end in order to accomplish this function, i.e. to enable it to securely couple to an optional introducer tube.

In this first embodiment of a system of the present invention, hollow elongate shaft 184 is manufactured out of polyimide, which provides exceptional electrical insulation while maintaining sufficient flexibility and compactness. In alternate embodiments, hollow elongate shaft 184 may be any other material imparting similar qualities. In still other embodiments, hollow elongate shaft 184 may be manufactured from an electrically conductive material and may be covered by an insulating material so that delivered energy remains concentrated at energy delivery device 192 of distal tip region 190. In the first embodiment, probe assembly 106 comprises a marker 384 at some point along handle 180 or along the length of elongate hollow shaft 184. In an embodiment where a probe assembly 106 is inserted into an optional introducer tube, marker 384 may be located on elongate hollow shaft 184 (as shown in FIG. 3) and may be a visual depth marker that functions to indicate when the distal tip of the probe assembly is located at a distal end of the introducer tube by aligning with a hub of the introducer tube. Marker 384 will thus provide a visual indication as to the location of the distal tip of a probe assembly 106 relative to an optional introducer tube. Alternatively, marker 384 may be a tactile marker and may be used to indicate the orientation of a particular component of probe assembly 106. For example, as discussed below, probe assembly 106 may comprise a secondary temperature sensor. In such an embodiment, marker 384 may serve to indicate the radial location of the secondary temperature sensor within probe assembly 106.

Referring in detail to FIG. 4, a perspective cut-away view of a first embodiment of distal tip region 190 of probe assembly 106 is shown. In this embodiment, distal tip region 190 comprises one or more temperature sensing elements 402 which are operable to measure the temperature at and proximate to the one or more energy delivery devices 192. The one or more temperature sensing elements 402 may comprise one or more thermocouples, thermometers, thermistors, optical fluorescent sensors or any other means of sensing temperature. In the first embodiment, the one or more temperature sensing elements 402 are connected to generator 102 via probe assembly cable 170 and cable 104 although any means of communication between the one or more temperature sensing elements 402 and generator 102, including wireless protocols, are included within the scope of the present invention. In the embodiment illustrated by FIG. 4, one or more temperature sensing elements 402 comprises a thermocouple junction made by joining a stainless steel hypotube 406 to a constantan wire 410, wherein constantan wire 410 is insulated by wire insulation 412. In this embodiment, the junction of hypotube 406 and constantan wire 410 is made by laser welding, although any other means of joining two metals may be used. Furthermore, in this embodiment, hypotube 406 and constantan wire 410 extend through a lumen of hollow elongate shaft 184 and connect to probe assembly cable 170 within handle 180. In the embodiment shown in FIG. 4, the one or more temperature sensing elements 402 protrudes beyond the one or more energy delivery devices 192. In this specific embodiment, whereby temperature sensing element 402 comprises a stainless steel hypotube 406, stainless steel hypotube 406 may be electrically conductive and may be electrically coupled to the one or more energy delivery devices 192. Thus, in such an embodiment whereby energy may be conducted to the protrusion and delivered from the protrusion to surrounding tissue, the protrusion may be understood to be a component of both temperature sensing element 402 as well as the one or more energy delivery devices 192. Placing the one or more temperature sensing elements 402 at this location, rather than within lumen 450 defined by the one or more energy delivery devices 192, is beneficial because it allows the one or more temperature sensing elements 402 to provide a more accurate indication of the temperature of tissue proximate to the one or more energy delivery devices 192. This is due to the fact that, when extended beyond the one or more energy delivery devices 192, the one or more temperature sensing elements 402 will not be as affected by the cooling fluid flowing within a lumen 450 as it would be were it located within lumen 450. Thus, in this embodiment of the present invention, probe assembly 106 comprises a protrusion protruding from the distal region of the probe assembly, whereby the protrusion is a component of temperature sensing element 402.

In the first embodiment of a probe assembly of the present invention, probe assembly 106 further comprises one or more secondary temperature sensing elements 404 located within hollow elongate shaft 184 at some distance away from one or more energy devices 192, and positioned adjacent a wall of hollow elongate shaft 184. For example, if the one or more energy delivery devices 192 comprises an electrode that is 5-7 mm in length, then locating a secondary temperature sensing element 404 approximately 3 mm away from a proximal end of said electrode is optimal for measuring temperature at the periphery of an intervertebral disc as is discussed in more detail below. As mentioned above with respect to the one or more temperature sensing elements 402, the one or more secondary temperature sensing elements 404 may similarly comprise one or more thermocouples, thermometers, thermistors, optical fluorescent sensors or any other means of sensing temperature. In the first embodiment illustrated by FIG. 4, the secondary temperature sensing element 404 is a thermocouple made by joining copper and constantan thermocouple wires, designated as 420 and 422 respectively. As mentioned earlier with respect to the one or more temperature sensing elements 402, the copper and constantan wires 420 and 422 may extend through a lumen of hollow elongate shaft 184 and may connect to probe assembly cable 170 within handle 180.

Probe assembly 106 may further comprise a thermal insulator 430 located proximate to any of the one or more temperature sensing elements 402 or the one or more secondary temperature sensing elements 404. Thermal insulator 430 may be made from any thermally insulating material, for example silicone, and may be used to insulate any temperature sensing element from other components of probe assembly 106, so that the temperature sensing element will be able to more accurately measure the temperature of the surrounding tissue. In the first embodiment illustrated by FIG. 4, thermal insulator 430 is used to insulate the one or more secondary temperature sensing elements 404 from cooling fluid passing through shaft supply tube 302 and shaft return tube 304.

As an additional feature of a first embodiment of a system of the present invention, probe assembly 106 comprises a radiopaque marker 440 incorporated somewhere along hollow elongate shaft 184. For example, an optimal location for a radiopaque marker may be at or proximate to distal tip region 190, adjacent the one or more energy delivery devices 192 as shown in FIG. 4. Radiopaque markers are visible on fluoroscopic x-ray images and can be used as visual aids when attempting to place devices accurately within a patient's body. These markers can be made of many different materials, as long as they possess sufficient radiopacity. Suitable materials include, but are not limited to silver, gold, platinum and other high-density metals as well as radiopaque polymeric compounds. Various methods for incorporating radiopaque markers into or onto medical devices may be used, and the present invention is not limited in this regard.

In the first embodiment of a system of the present invention, radiopaque marker 440 may comprise silver solder placed within hollow elongate shaft 184, proximate to the one or more energy delivery devices 192. When viewed under x-ray fluoroscopy, the silver solder will appear dark, allowing a user to readily distinguish the location of the solder. If the solder is placed proximate to the one or more energy delivery devices 192, then the one or more energy delivery devices 192 will be distinguishable relative to other regions of hollow elongate shaft 184, allowing for accurate positioning of the one or more energy delivery devices 192 at a treatment site within a body of a patient. Radiopaque markers 440 may also be incorporated by other methods, including but not limited to vapor deposition, ion implantation, dip coating, metal plating and electro-plating. Further, there may be more than one radiopaque marker 440 associated with probe assembly 106.

Figure 5A:
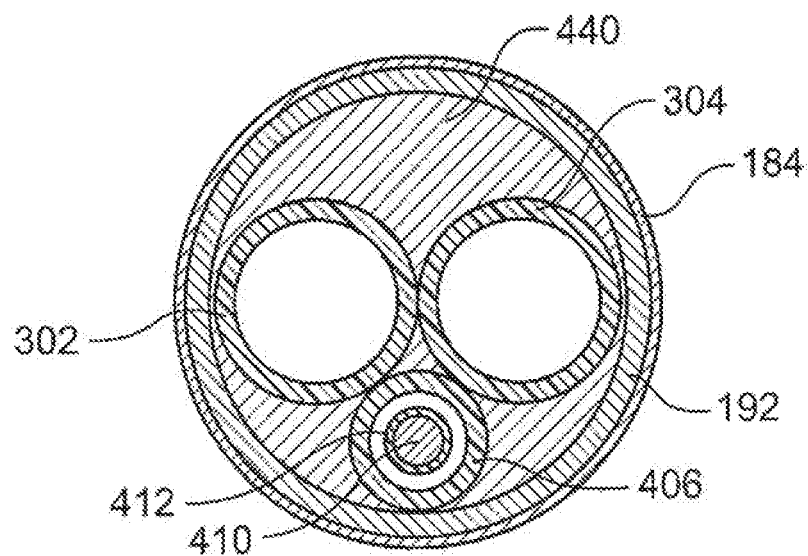
FIG. 5A is an axial cross-section through the distal tip region of the probe assembly shown in FIG. 4.
Figure 5B:
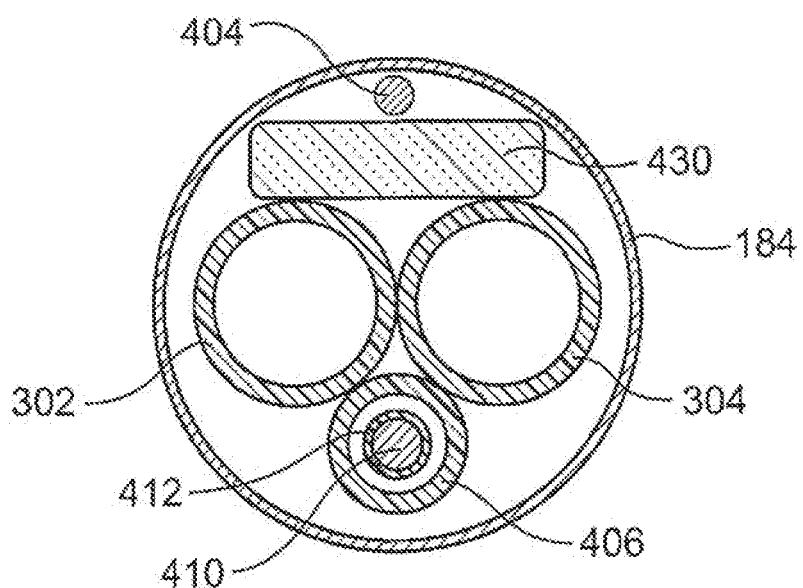
FIG. 5B is an axial cross-section through a more proximal portion of the distal tip region of the probe assembly shown in FIG. 4.

Cross-sectional views of portions of distal tip region 190, as indicated in FIG. 4, are shown in FIGS. 5A and 5B. Referring first to FIG. 5A, three hypotubes 302, 304, and 406 are positioned within a lumen 450 defined by hollow elongate shaft 184 and the one or more energy delivery devices 192. Shaft supply tube 302 and shaft return tube 304 carry cooling fluid to and from the distal end of distal tip region 190, respectively. In this embodiment, hypotube 406 is made of a conductive material such as stainless steel and is operable to transmit energy from probe assembly cable 170 to the one or more energy delivery devices 192. In addition, hypotube 406 defines a lumen within which a means of connecting the one or more temperature sensing devices 402 to probe assembly cable 170 may be located. For example, if the one or more temperature sensing devices 402 comprises a thermocouple, then a constantan wire 410 may extend from probe assembly cable 170 to the thermocouple junction through hypotube 406 as is shown in FIG. 4. Alternatively, more than one wire may be passed through the lumen of hypotube 406 or the lumen of hypotube 406 may be utilized for another purpose.

In the first embodiment of the present invention, the one or more energy delivery devices 192 is an electrode, as discussed above. FIG. 5A is a cross-section of a portion of distal tip region 190 wherein hollow elongate shaft 184 and electrode 192 overlap in order to secure the electrode in place. In this embodiment, the lumen defined by hollow elongate shaft 184 and electrode 192 at this portion of distal tip region 190, contains a radiopaque marker 440 comprised of silver solder, as discussed above. The silver solder fills the lumen such that any cooling fluid supplied to probe assembly 106, that is not located within one of the cooling tubes described earlier, is confined to the distal tip region 190 of probe assembly 106. Thus, in this embodiment, the silver solder may be referred to as a flow impeding structure since it functions to restrict the circulation of fluid to a specific portion (in this case, at least a portion of distal region 190) of probe assembly 106. In other words, cooling fluid may flow from the one or more cooling devices 108, through the cooling supply tubes described earlier, to distal tip region 190 of probe assembly 106. The cooling fluid may then circulate within lumen 450 defined by electrode 192 in order to provide cooling to the electrode. In the context of the present invention, an internally-cooled probe is defined as a probe having such a configuration, whereby a cooling medium does not exit probe assembly 106 from a distal region of probe assembly 106. The cooling fluid may not circulate further down hollow elongate shaft 184 due to the presence of the silver solder, and flows through the cooling return tubes described earlier back to the one or more cooling devices 108. In alternate embodiments, other materials may be used instead of silver solder, and the invention is not limited in this regard.

Referring now to FIG. 5B, a cross-section of a portion of distal tip region 190, proximal from the cross-section of FIG. 5A as illustrated in FIG. 4, is shown. In the embodiment illustrated by FIG. 5B, the one or more secondary temperature sensing elements 404 is located proximate to an inner wall of hollow elongate shaft 184. This proximity allows the one or more secondary temperature sensing elements 404 to provide a more accurate indication of the temperature of surrounding tissue. In other words, the one or more secondary temperature sensing elements 404 may be operable to measure the temperature of the inner wall of hollow elongate shaft 184 at the location of the one or more secondary temperature sensing elements 404. This temperature is indicative of the temperature of tissue located proximate to the outer wall of hollow elongate shaft 184. Thus, it is beneficial to have the one or more secondary temperature sensing elements 404 located proximate to an inner wall of hollow elongate shaft 184, rather than further away from the inner wall.

As described above, thermal insulator 430 is placed between the one or more secondary temperature sensing elements 404 and shaft supply and return tubes 302 and 304 in the first embodiment of the present invention. This serves to insulate the one or more secondary temperature sensing elements 404 from the cooling effect of the cooling fluid located within shaft supply tube 302 and shaft return tube 304. Thus, by minimizing the cooling effect, one or more secondary temperature sensing elements 404 is able to provide a more accurate indication as to the surrounding tissue temperature.

FIGS. 5A and 5B also illustrate the relative positions of the three hypotubes used in a first embodiment of a system of the present invention. In this embodiment, the three hypotubes are held together in some fashion in order to increase the strength of probe assembly 106. For example, the three hypotubes may be bound together temporarily or may be more permanently connected using solder, welding or any suitable adhesive means. Various means of binding and connecting hypotubes are well known in the art and the present invention is not intended to be limited in this regard.

As stated earlier, the figures included in this application, which illustrate some embodiments of a system of the present invention, are intended to be exemplary only. For example, with respect to FIG. 5A, the relative positions of the three hypotubes as shown are not intended to limit the scope of the invention in any way. It will be readily apparent to those skilled in the art that many variations are possible, relating to both the number as well as the position of the hypotubes, all of which are included within the scope of the present invention. In alternate embodiments, the shape of the hypotubes may be optimized so that more efficient use is made of a lumen defined by hollow elongate shaft 184 and the one or more energy delivery devices 192. In yet further embodiments, distal cooling supply tube 162 may provide cooling to the one or more energy delivery devices 192 without the use of hypotubes, and this invention is intended to include any means of supplying cooling to and returning cooling from distal tip region 190, as well as any and all means of transmitting energy between probe assembly cable 170 and the one or more energy delivery devices 192. For example, one or more cooling devices 108 may comprise an electrothermal cooling device, as mentioned above. In such embodiments, the mechanism of supplying cooling to the one or more energy delivery devices 192 may differ significantly from the illustrated embodiment but is nevertheless included within the scope of the present invention.

As described above, providing cooling to probe assemblies 106 allows heat delivered through energy delivery devices 192 to be translated further into the tissue without raising the temperature of the tissue immediately adjacent energy delivery device 192. FIGS. 6A-6C illustrate various embodiments for the internal cooling of distal tip region 190 of probe assembly 106. Arrows 408, 630, and 660 indicate the direction of flow of the cooling liquid in FIGS. 6A, 6B, and 6C, respectively. FIG. 6A shows a longitudinal cross-section of an internal liquid cooled distal tip region 190 of the first embodiment of the present invention, as shown in FIG. 4. As described previously, the cooling supply mechanism comprises two hypotubes, shaft supply tube 302 and shaft return tube 304. In FIG. 6B, the cooling supply mechanism comprises a single hypotube 600 defining a central bore 610 and an outer annular passageway 620. Cooling liquid passes down the central bore 610, as indicated by arrow 630, and passes back through the outer annular passageway 620.

FIG. 6C shows a cooling supply mechanism configured similarly to that shown in FIG. 6B. However, in this embodiment, a single hypotube 640 defines one or more apertures 650 proximate a distal tip region 190. Apertures 650 direct the flow of cooling liquid outward towards outer annular passageway 620. In this embodiment, hypotube 640 may be made of a conductive material such as constantan and may be welded to energy delivery device 192 which may be made of a different conductive material such as stainless steel. In this way, a junction between hypotube 640 and energy delivery device 192 acts as a thermocouple useful to measure temperature, in addition to providing channels for the flow of cooling liquid.

FIG. 7 shows a longitudinal cross-section of an embodiment of a distal tip region 190 further comprising an insulated impedance measuring tip 700 adjacent the distal end of energy delivery device 192. Impedance measuring tip 700 can be used to help determine a position of energy delivery device 192 while the probe assembly 106 is being inserted into a region of tissue. Impedance measuring tip 700 may be operable to send very small pulses of low power, high frequency current through the tissue to a dispersive ground electrode on the surface of the patient's skin (not shown), or may be used in any other way of measuring impedance known in the art. Insulating material 710 isolates impedance measuring tip 700 from energy delivery device 192. As probe assembly 106 is moved through tissue, the impedance of the tissue can be measured, allowing the location of energy delivery device 192 to be determined. For example, when impedance measuring tip 700 moves from the annulus fibrosis to the nucleus pulposus of an intervertebral disc, the impedance level will drop. This drop in impedance effectively indicates that energy delivery device 192 is located within the annulus fibrosis since energy delivery device 192 is located proximally from impedance measuring tip 700 and is isolated from impedance measuring tip 700 by insulating material 710. It will be understood to persons skilled in the art that the embodiments of the invention in which distal tip region 190 comprises an impedance measuring tip will also include internal conduits to hold wires that connect the impedance measuring tip to the generator 102.

In some embodiments (not shown), distal tip region 190 may further be configured to predominantly expose one side of energy delivery device 192, allowing increased control of the direction of energy delivery (not shown). This could be accomplished by incorporating an electrically insulating material into some regions of the energy delivery device, or through an associated insulation sleeve.

As mentioned above, system 100 of the present invention may further comprise one or more introducer tubes. Generally, introducer tubes may comprise a proximal end, a distal end and a longitudinal bore extending therebetween. As previously stated with respect to a first embodiment of the present invention, introducer tubes (when used) are operable to easily and securely couple with probe assembly 106. For example, the proximal end of the introducer tubes may be fitted with a connector able to mate reversibly with handle 180 of probe assembly 106. An introducer tube may be used to gain access to a treatment site within a patient's body and a hollow elongate shaft 184 of a probe assembly 106 may be introduced to said treatment site through the longitudinal bore of said introducer tube. Introducer tubes may further comprise one or more depth markers in order to enable a user to determine the depth of the distal end of the introducer tube within a patient's body. Additionally, introducer tubes may comprise one or more radiopaque markers to ensure the correct placement of the introducers when using fluoroscopic guidance.

In embodiments of the invention that include one or more introducer tubes, the one or more introducer tubes may comprise one or more temperature sensors along their lengths. In such embodiments, the one or more temperature sensors may be placed proximate to the distal end of the one more introducer tubes so as to enable the one or more temperature sensors to measure the temperature of tissue surrounding the distal end of the one or more introducer tubes. For example, if a system of the present invention, comprising introducer tubes, is used in a treatment procedure of an intervertebral disc, a temperature sensing element located proximate to the distal end of the introducer tube may be capable of monitoring the temperature of the periphery of the intervertebral disc, or of tissue surrounding the disc, when the introducer tube is inserted into the disc. In other embodiments, multiple temperature sensing elements disposed along the introducer may be used to indicate the size of the lesion as it expands. This may be particularly useful in the treatment of tumor tissue, for example.

Introducer tubes may be made of various materials, as is known in the art and, if said material is electrically conductive, the introducer tubes may be electrically insulated along all or part of their length, in order to prevent energy from being conducted to undesirable locations within a patient's body. In some embodiments, hollow elongate shaft 184 may be electrically conductive, and an introducer may function to insulate the shaft leaving the energy delivery device 192 exposed for treatment. Further, the one or more introducer tubes may be operable to connect to a power source and may therefore form part of an electrical current impedance monitor (wherein at least a portion of the introducer tube is not electrically insulated). Different tissues may have different electrical impedance characteristics and it is therefore possible to determine tissue type based on impedance measurements, as has been described. Thus, it would be beneficial to have a means of measuring impedance in order to determine the tissue within which a device is located. In addition, the gauge of the introducer tubes may vary depending on the procedure being performed and/or the tissue being treated. In one particular embodiment, the introducer tubes should be sufficiently sized in the radial dimension so as to accept at least one probe assembly 106. In embodiments of a system of the present invention lacking introducer tubes, hollow elongate shaft 184 may be insulated (in embodiments where hollow elongate shaft 184 is made of a conductive material) for the aforementioned reason, i.e. so as not to conduct energy to portions of a patient's body that are not being treated. Introducers may be manufactured from Inconel or a similar non-magnetic metal to allow MRI- or CT-assisted placement.

In some embodiments of a system of the present invention comprising one or more introducer tubes, the system may further comprise one or more stylets. A stylet may have a beveled tip to facilitate insertion of the one or more introducer tubes into a patient's body. Various forms of stylets are well known in the art and the present invention is not limited is to include only one specific form. Further, as described above with respect to the introducer tubes, the one or more stylets may be operable to connect to a power source and may therefore form part of an electrical current impedance monitor. In other embodiments, one or more probe assemblies 106 may form part of an electrical current impedance monitor, as has been mentioned with respect to FIG. 7. Thus, generator 102 may receive impedance measurements from one or more of one or more stylets, one or more introducer tubes and one or more probe assemblies 106 and may perform an action, such as alerting a user to an incorrect placement of an energy delivery device 192, based on the impedance measurements.

In a first embodiment of a system of the present invention, first and second probe assemblies 106 are operated in a bipolar mode. In this embodiment, electrical energy is delivered to first and second probe assemblies 106 and this energy is preferentially concentrated between first and second probe assemblies 106 through a region of tissue to be treated, as is discussed in greater detail below. The region of tissue to be treated is thus heated by the energy concentrated between first and second probe assemblies 106. In other embodiments, first and second probe assemblies 106 may be operated in a monopolar mode, in which case an additional grounding pad would be required on the surface of a body of a patient, as is known in the art. Any combination of bipolar and monopolar procedures may also be used.

In alternate embodiments, a system of the present invention may comprise more than two probe assemblies. For example, in some embodiments, three probe assemblies may be used and the probe assemblies may be operated in a triphasic mode, whereby the phase of the current being supplied differs for each probe assembly.

As another feature of the present invention, a system may be configured to control one or more of the flow of current between electrically conductive components and the current density around a particular component. For example, a system of the present invention may comprise three electrically conductive components, including two of similar or identical dimensions and a third of a larger dimension, sufficient to act as a dispersive electrode. Each of the electrically conductive components should beneficially be operable to transmit energy between a patient's body and an energy source. Thus, two of the electrically conductive components may be probe assemblies while the third electrically conductive component may function as a grounding pad or dispersive/return electrode. In one embodiment, the dispersive electrode and a first probe assembly are connected to a same electric pole while a second probe assembly is connected to the opposite electric pole. In such a configuration, electrical current may flow between the two probe assemblies or between the second probe assembly and the dispersive electrode. In order to control the current to flow preferentially to either the first probe assembly or the dispersive electrode, a resistance or impedance between one or more of these conductive components (i.e. the first probe assembly and the dispersive electrode) and a current sink (e.g. circuit 'ground') may be varied. In other words, if it would be desirable to have current flow preferentially between the second probe assembly and the dispersive electrode (as in a monopolar configuration), then the resistance or impedance between the first probe assembly and the circuit 'ground' may be increased so that the current will prefer to flow through the dispersive electrode to 'ground' rather than through the first probe assembly (since electrical current preferentially follows a path of least resistance). This may be useful in situations where it would be desirable to increase the current density around the second probe assembly and/or decrease the current density around the first probe assembly. Similarly, if it would be desirable to have current flow preferentially between the second probe assembly and the first probe assembly (as in a bipolar configuration), then the resistance or impedance between the dispersive electrode and 'ground' may be increased so that the current will prefer to flow through the first probe assembly to 'ground' rather than through the dispersive electrode. This would be desirable when a standard bipolar lesion should be formed. Alternatively, it may desirable to have a certain amount of current flow between the second probe assembly and the first probe assembly with the remainder of current flowing from the second probe assembly to the dispersive electrode (a quasi-bipolar configuration). This may be accomplished by varying the impedance between at least one of the first probe assembly and the dispersive electrode, and 'ground', so that more or less current will flow along a desired path. This would allow a user to achieve a specific, desired current density around a probe assembly. Thus, this feature of the present invention may allow a system to be alternated between monopolar configurations, bipolar configurations or quasi-bipolar configurations during the course of a treatment procedure.

As a further example of this feature of the present invention, four electrically conductive components may be provided. For example, a system may comprise two probe assemblies as well as two dispersive electrodes and each electric pole may be connected to a single probe assembly and a single dispersive electrode. As was mentioned in the previous example, the resistance or impedance between any of the electrically conductive components and a current sink (e.g. circuit 'ground') can be altered in order to control the flow of current between components. This configuration would be useful to selectively control current density around each probe assembly and thus selectively control tissue temperature and electrical field properties.

In yet another example of this feature, three substantially identical electrically conductive components, for example three probe assemblies, may be provided. In such a configuration, first and second probe assemblies may be connected to a single electric pole while a third probe assembly may be connected to the opposite electrical pole. In such an embodiment, the direction of current flow may be changed during the course of the procedure by varying the resistance or impedance between each of the first and second probe assemblies and 'ground'. Thus, current may flow in a bipolar fashion between the third probe assembly and either the first or second probe assemblies, depending on which probe assembly provides a higher resistance or impedance to the current flow. This system may be useful to alter the size or shape of a treatment area or lesion within a bodily tissue. Different energy modes as are known in the art may also be used depending on whether it is desired to cut or coagulate the tissue.

Figure 8:
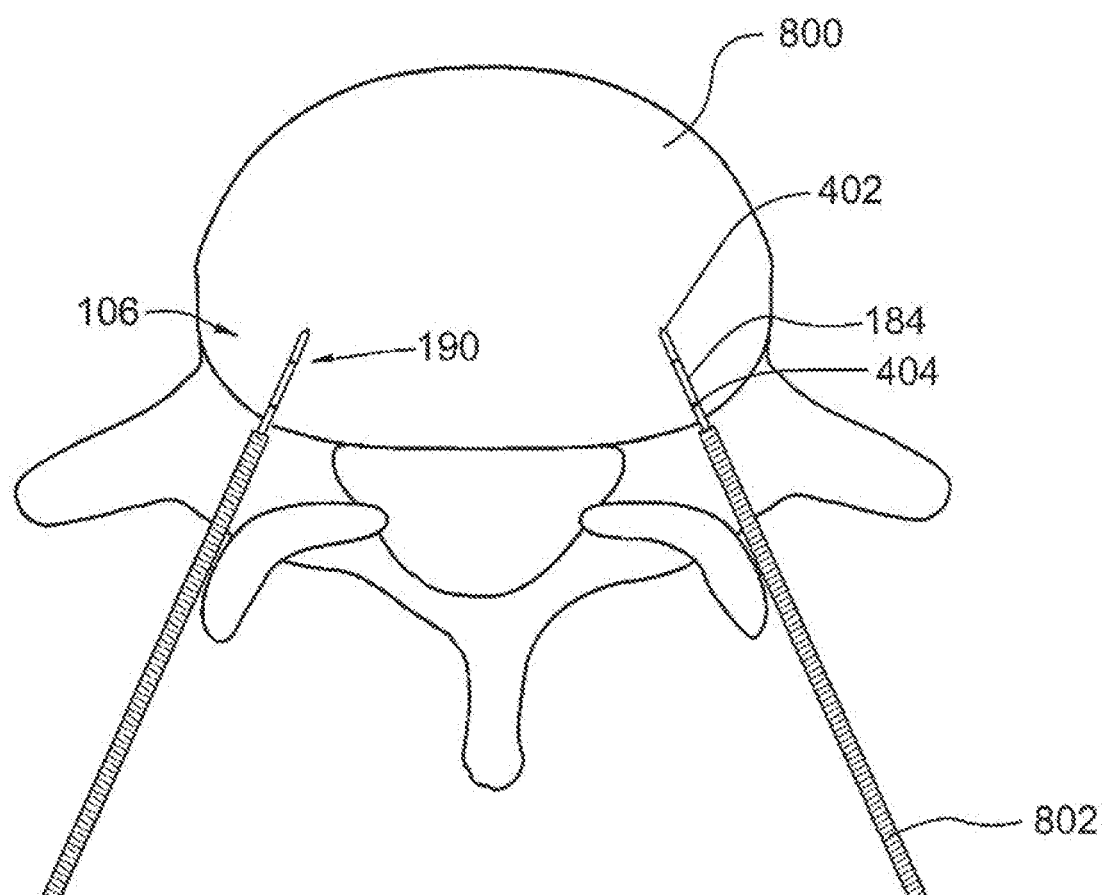
FIG. 8 shows two probes placed within an intervertebral disc.

As has been described, a system of the present invention optionally comprises two or more temperature sensing elements, for example, one associated with the one or more energy delivery devices 192 and a second associated with one or more of hollow elongate shaft 184 or an introducer tube. A secondary temperature sensing element may also be located on a separate device inserted into the patient's body. FIG. 8 illustrates an example of the utility of having two spaced-apart temperature sensors. Two probe assemblies 106 are shown placed within introducer tubes 802, wherein distal tip regions 190 of probe assemblies 106 are located within an intervertebral disc 800. Each of probe assemblies 106 comprises a hollow elongate shaft 184, an energy delivery device 192, a temperature sensing element 402 and a secondary temperature sensing element 404. Temperature sensing element 402 measures the tissue temperature at or proximate to energy delivery device 192 and, although temperature sensing element 402 is shown to be protruding from the distal tip of energy delivery device 192, it will be clear to those skilled in the art that it may also be placed at other locations associated with energy delivery device 192 (for example, protruding from one side of energy delivery device 192). In this embodiment, secondary temperature sensing element 404 is located within hollow elongate shaft 184 or alternatively on the surface of hollow elongate shaft 184. In either case, secondary temperature sensing element 404 is operable to measure the temperature of tissue at the periphery of the disc as illustrated in FIG. 8. Thus, in addition to measuring the temperature at or proximate to energy delivery device 192, the temperature of tissue at the periphery of the disc is measured as well. Measuring peripheral disc temperature may be beneficial in order to ensure that tissue at the disc periphery or external to the disc is not being overheated. FIG. 8 is intended to illustrate the utility of having more than one temperature sensor and is intended to be exemplary only. The number and positions of the temperature sensors and the benefits of having more than one temperature sensor are not limited to cooled probes and may differ depending on the application.

FIG. 9A illustrates an embodiment whereby a temperature sensor 900 is located, via extrusion or another process, in a wall of hollow elongate shaft 184. By locating a temperature sensor at this position, the temperature of the tissue surrounding the shaft can be measured as is well understood by a person skilled in the art. Alternatively, temperature sensing elements may be located within probe assembly 106 so as to measure the temperature of inflow and outflow of cooling fluid. By measuring the change in temperature of the inflow and outflow cooling fluid, the temperature of the tissue located adjacent energy delivery device 192 can be determined. In further embodiments, temperature sensing elements may be positioned in any other location as needed. For example, in a treatment procedure involving an intervertebral disc, temperature sensors not associated with probe assemblies 106 may be placed external to the disc, in the spinal canal, or in proximity to the spinal nerve.

FIG. 9B shows a distal tip region 190 of a probe assembly 106 with an extendible remote temperature sensing element 910 which may be deployed from probe assembly 106. The internal liquid cooling system has been omitted for ease of illustration. Temperature sensing element 910 allows monitoring of the temperature within tissues located remotely from the surface of energy delivery device 192. Temperature sensing element 910 may be steerable so that its position may be changed during a procedure to obtain temperature measurements from a variety of tissue regions. In such an embodiment, the cooling feedback may be determined by a combination of temperatures within or surrounding the tissue being treated.

Any or all of the above embodiments of probe assembly 106 may comprise an active shape control mechanism to steer distal tip region 190, for example as it is moved through the tissue. Such active shape control mechanisms include, but are not limited to, cables for a mechanical actuator, hydraulic or piezo-electric devices, and solenoids.

Usage of a first embodiment of a system 100 of the present invention to treat an intervertebral disc may be described generally as follows: With a patient lying on a radiolucent table, fluoroscopic guidance is used to percutaneously insert an introducer with a stylet to access the posterior of an intervertebral disc. In addition to fluoroscopy, other aids, including but not limited to impedance monitoring and tactile feedback, may be used to assist a user to position the introducer or probe assemblies within the patient's body. The use of impedance monitoring has been described earlier, whereby a user may distinguish between tissues by monitoring impedance as a device is inserted into the patient's body. With respect to tactile feedback, different tissues may offer different amounts of physical resistance to an insertional force. This allows a user to distinguish between different tissues by feeling the force required to insert a device through a given tissue. One method of accessing the disc is the extrapedicular approach in which the introducer passes just lateral to the pedicle, but other approaches may be used. A second introducer with stylet is then placed contralateral to the first introducer in the same manner, and the stylets are removed. Probe assemblies 106 are inserted into each of the two introducers placing electrodes 192 in the disc such that the distance between electrodes 192 is 1 mm to 55 mm. Once in place, a stimulating electrical signal may be emitted from either of electrodes 192 to a dispersive electrode or to the other electrode 192. This signal may be used to stimulate sensory nerves where replication of symptomatic pain would verify that the disc is pain-causing. A different signal may be used to stimulate motor nerves where a motor reaction indicates unsafe proximity to motor nerves that should not be heated. Probe assemblies 106 are connected to an RF generator 102 as well as to peristaltic pumps 108 to cool distal tip regions 190. Radio frequency energy is delivered to electrodes 192 and the power is altered according to the temperature measured by temperature sensing element 402 in the tip of electrode 192 such that a desired temperature is reached between the distal tip regions 190 of the two probe assemblies 106. During the course of the procedure, a treatment protocol such as the cooling supplied to the probe assemblies 106 and/or the power transmitted to the probe assemblies 106 may be adjusted in order to maintain a desirable treatment area shape, size and uniformity. These adjustments may be made on the basis of feedback from various sources, including but not limited to temperature sensors and impedance sensors. In addition, the treatment protocols may be adjusted based on an error signal received by a control module, which control module may be associated with generator 102. The cooling devices may be independently controlled to alter the rate of cooling to each electrode 192.

Following treatment, energy delivery and cooling are stopped and probe assemblies 106 are removed from introducers. A fluid such as an antibiotic, an anesthetic or a contrast agent may be injected through the introducers, followed by removal of the introducers. Alternatively, the distal tips of the probe assemblies 106 may be sharp and sufficiently strong to pierce tissue so that introducers may not be required. As mentioned above, positioning probe assemblies 106, and more specifically energy delivery devices 192, within the patient's body, may be assisted by various means, including but not limited to fluoroscopic imaging, impedance monitoring and tactile feedback. Additionally, some embodiments of this method aspect may comprise one or more steps of inserting or removing material into a patient's body. For example, as has been described, a fluid may be inserted through an introducer tube during the course of a treatment procedure. Alternatively, a substance may be inserted through probe assembly 106, in embodiments where probe assembly 106 comprises an aperture in fluid communication with a patient's body. Furthermore, material may be removed from the patient's body during the course of the treatment procedure. Such material may include, for example, damaged tissue, nuclear tissue and bodily fluids. Possible treatment effects include, but are not limited to, coagulation of nerve structures (nociceptors or nerve fibers), ablation of collagen, biochemical alteration, upregulation of heatshock proteins, alteration of enzymes, and alteration of nutrient supply.

A system of the present invention may be used in various medical procedures where usage of an energy delivery device may prove beneficial. Specifically, a system of the present invention is particularly useful for procedures involving treatment of back pain, including but not limited to treatments of tumors, intervertebral discs, facet joint denervation, sacroiliac joint lesioning or intraosseous (within the bone) treatment procedures. Moreover, the system is particularly useful to strengthen the annulus fibrosus, shrink annular fissures and impede them from progressing, cauterize granulation tissue in annular fissures, and denature pain-causing enzymes in nucleus pulposus tissue that has migrated to annular fissures. Additionally, the system may be operated to treat a herniated or internally disrupted disc with a minimally invasive technique that delivers sufficient energy to the annulus fibrosus to breakdown or cause a change in function of selective nerve structures in the intervertebral disc, modify collagen fibrils with predictable accuracy, treat endplates of a disc, and accurately reduce the volume of intervertebral disc tissue. The system is also useful to coagulate blood vessels and increase the production of heat shock proteins.

As an illustration of the benefits of using a system of the present invention, some of the aforementioned procedures will now be described in more detail. Although some of the figures and the description relate to the percutaneous insertion of the probes into an intervertebral disc it will be understood that the probes can also be used during surgery and can be inserted directly into a disc or other tissue through an open cavity.

Figure 11A:
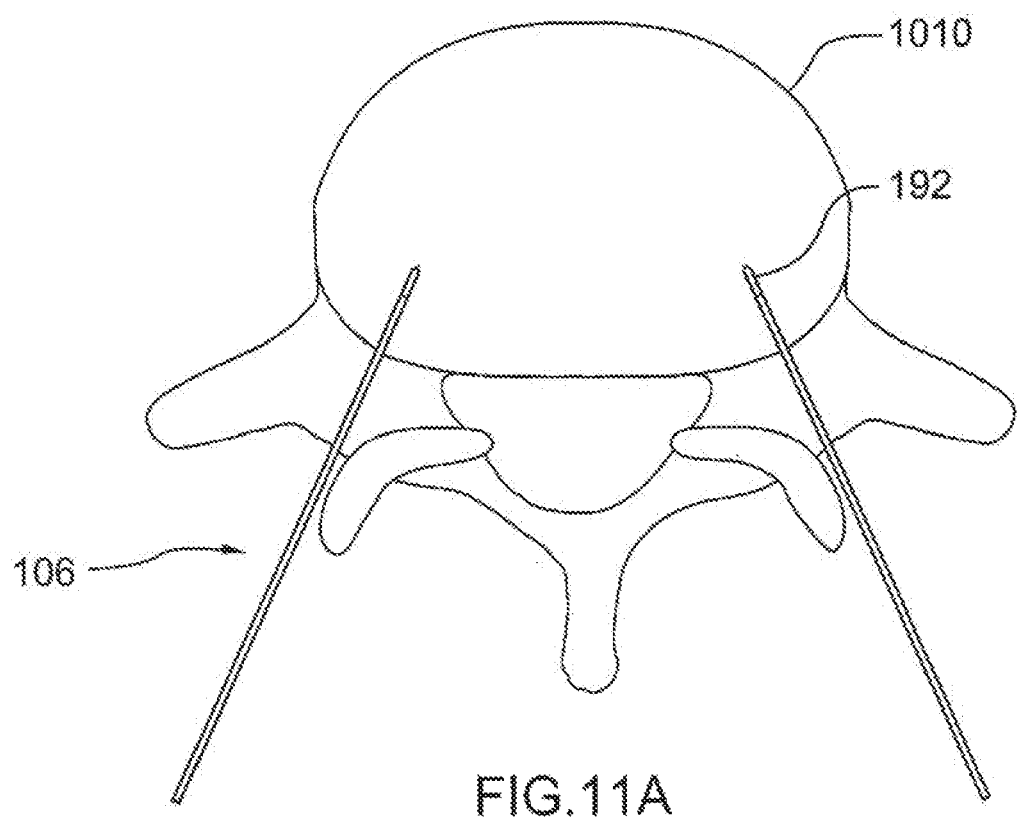
FIGS. 11A and 11B show possible placements of two probe assemblies in an intervertebral disc.
Figure 11B:
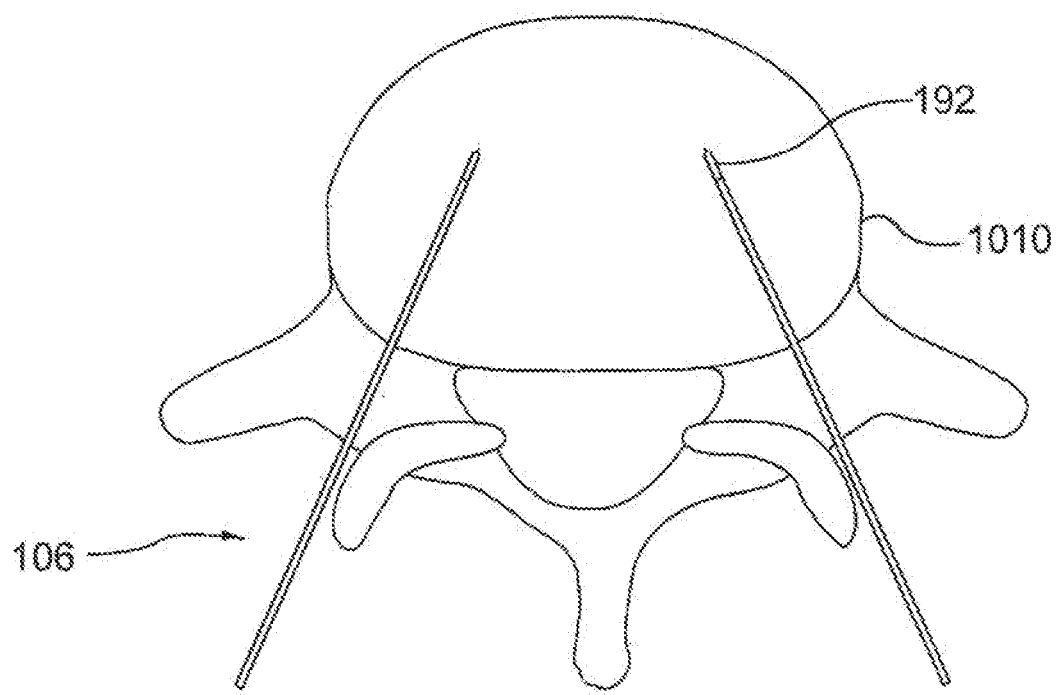

Treatment of an intervertebral disc has already been mentioned briefly, but will now be described in more detail. FIG. 10 shows a lateral view of a portion of a human spine with vertebrae 1000 and intervertebral discs 1010 showing the location of the nucleus pulposus 1020 in dashed outline surrounded by overlapping layers of the annulus fibrosus. FIGS. 11A and 11B are cross-sections through the intervertebral disc as indicated in FIG. 10. In the embodiment of the procedure shown in FIG. 11A, energy delivery devices 192 of two probe assemblies 106 are located partially in the nucleus pulposus and partially in the annulus fibrosis of intervertebral disc 1010 so that at least an equal amount of energy is delivered to the nucleus pulposus as to the annulus fibrosis. An alternate placement of probe assemblies 106 towards the anterior of the intervertebral disc is illustrated in FIG. 11B. Placement of probe assemblies 106 in this region of the disc could be used for treating anterior fissures or for various other applications in the anterior region of the disc. Alternatively, for some procedures, one probe assembly 106 may be placed in the anterior and one in the posterior of the disc. Other placements are possible for probe assemblies 106 depending on the desired treatment, and the invention is not intended to be limiting in this regard.

Proper positioning of the probe assemblies 106 may be determined using radiopaque markers associated with the introducer, stylet or probe assembly, or any combination thereof. Positioning may be further confirmed by injecting a small amount of radiopaque contrast solution into the disc. The optimal distance between probe assemblies 106 may vary according to disc location, disc size or geometry, hydration, degree of degeneration or other parameters. Motor and/or or sensory stimulation may be used before or after the procedure to confirm the location of the probe assemblies and the success of the procedure. Such stimulation may be done in monopolar or bipolar modes, as described in greater detail below.

Using a system of the present invention is beneficial because the use of two probe assemblies 106 in a bipolar configuration allows for the creation of a relatively uniform lesion between the distal tip regions 190 of the two probes. Using liquid-cooled probe assemblies 106 with an appropriate feedback control system as described above also contributes to the uniformity of the treatment. Cooling distal tip regions 190 of probe assemblies 106 helps to prevent excessively high temperatures in these regions which may lead to tissue adhering to probe assemblies 106 as well as an increase in the impedance of tissue surrounding distal tip regions 190 of probe assemblies 106. Thus, by cooling distal tip regions 190 of probe assemblies 106, higher power can be delivered to tissue with a minimal risk of tissue charring at or immediately surrounding distal tip regions 190. Delivering higher power to energy delivery devices 192 allows tissue further away from the energy delivery devices 192 to reach a temperature high enough so as to create a lesion and thus the lesion will not be limited to a region of tissue immediately surrounding energy delivery devices 192 but will rather extend preferentially from an distal tip region 190 of one probe assembly 106 to the other.

Figure 12A:
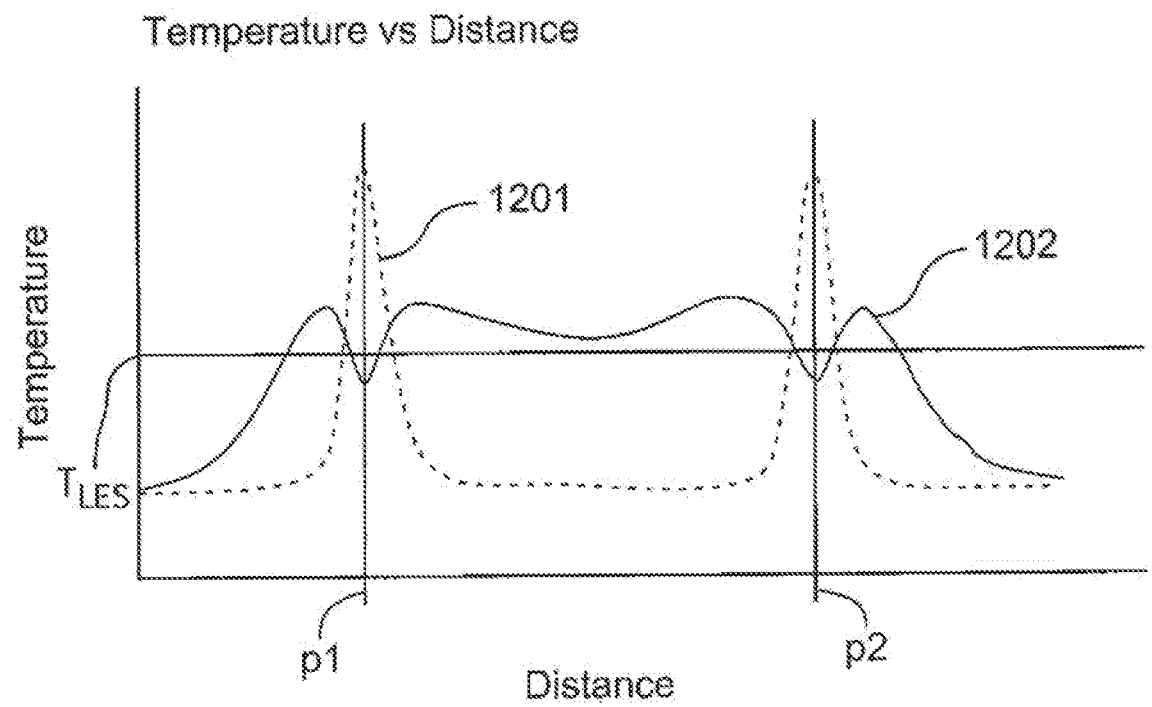
FIG. 12A is a graph of temperature in a uniform tissue vs. relative distance using cooled and non-cooled probe assemblies.
Figure 12B:
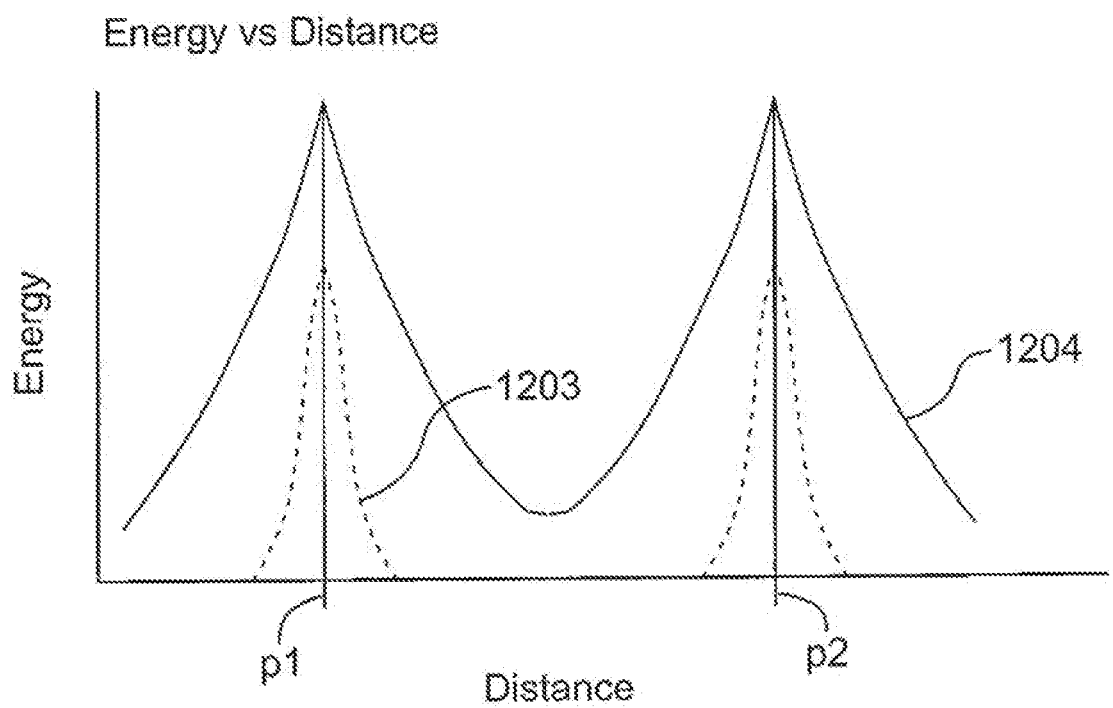
FIG. 12B is a graph of energy in a uniform tissue vs. relative distance using cooled and non-cooled probe assemblies.

This concept is illustrated in FIG. 12A, showing a graph of temperature vs. distance in a tissue with uniform thermal/electrical properties. The distal tip regions 190 of the two probe assemblies 106 are located at positions p1 and p2 on the x-axis and the temperature needed to create a lesion is noted as $T_{LES}$ on the y-axis. In FIGS. 12A and 12B, solid lines 1202 and 1204 represent a cooled probe assembly, while dashed lines 1201 and 1203 represent a non-cooled probe assembly. In order to create a lesion extending from p1 to p2, a large amount of power must be supplied to energy delivery devices 192 so that the energy will be transmitted over a far enough distance away from energy delivery devices 192 to create the lesion. Without the benefits of cooling, the higher the power that is supplied to energy delivery device 192, the higher the temperature around the energy delivery device 192 will be. Curve 1201 shows a temperature profile, as may be typically achieved using non-cooled probes in a uniform tissue. In such a configuration it is difficult to create a lesion extending from p1 to p2 because by supplying a large amount of power to energy delivery device 192, the temperature at the locations p1 and p2 of the distal tip regions reaches very high levels. High temperatures at the distal tip regions may cause nearby tissue to char and possibly adhere to distal tip regions 190. Furthermore, raising the temperature of tissue causes the impedance of the tissue to increase and limits the penetration of current into the tissue, thereby limiting the size of the lesion that can be created. In contrast, cooled probe assemblies may be used to form a desired lesion between p1 and p2 while reducing such temperature effects. Curve 1202 shows a typical temperature profile for a uniform tissue as may be seen when using two cooled probe assemblies. The temperatures at the distal tip regions, p1 and p2, are reduced relative to the surrounding tissue due to the effect of the cooling. This allows for higher power to be transmitted to energy delivery devices 192 without concern for tissue charring. In addition, because the temperature of tissue surrounding energy delivery device 192 is reduced, the impedance of the surrounding tissue will not increase significantly and therefore current supplied by energy delivery device 192 can penetrate more deeply into the tissue. As illustrated in FIG. 12A, a lesion can therefore be created between p1 and p2 using cooled probe assemblies 106 due to the lower local temperatures at p1 and p2. Although FIG. 12A shows the temperature at p1 and p2 to be below the lesioning temperature, the cooling supplied to the cooled probe assemblies may be reduced or eliminated allowing the temperature of tissue around p1 and p2 to increase in order to complete the lesion between p1 and p2.

In certain procedures, treatment with radio frequency energy in the absence of tissue heating may be beneficial. For example, collagen production by chondrocytes has been shown to be increased by treatment with radio frequency energy. Alternatively, some other biochemical or biological effect may be produced. FIG. 12B depicts energy vs. relative distance in a similar graph to FIG.

12A, where curves 1203 and 1204 depict non-cooled and cooled probe assemblies, respectively. As described above, the use of cooled probe assemblies allows the user to deliver more energy to larger tissue areas while minimizing the heating effects on tissue surrounding distal tip regions 190.

A system of the present invention may also be used in intraosseous procedures. Such procedures can treat a tumor in the bone or to denervate a neural structure within the bone. In an intraosseous procedure, introducer tubes are generally used to gain access to the bone to be treated, for example, a vertebra of a spinal column. In the context of this description, denervation refers to any function that is performed on neural structures so as to intervene with the transmission of a sensory signal (including pain signals) in a nerve associated with said neural structure. As is the case with procedures related to intervertebral discs, two probes may be inserted to spaced-apart sites within a bone and energy may be delivered to energy delivery means located at the distal regions of the probes. One benefit of using two probe assemblies in a bipolar configuration, as in a system of the present invention, is that knowledge of the precise location of the tissue to be treated is not necessary. As has been mentioned, use of bipolar probes allows for a lesion to be created preferentially between the two energy delivery devices. Therefore, so long as the tissue to be treated (e.g. a tumor or a neural structure) is located substantially between the distal regions of the two probes, it will generally be affected by the treatment procedure. Further applications of a device and/or system of the present invention may include, but are not limited to, the treatment of tumors in other parts of the body or for cardiac ablation.

As an additional feature of the method aspect of the present invention, certain embodiments may further comprise a step of performing a function to map the neural pathways in the tissue or to determine the proximity of one of the energy delivery devices 192 to a neural structure and this step may occur one or more times throughout the course of the procedure. This step can involve, in one embodiment, stimulation of the neural tissue at one or more frequencies and subsequent observation to determine the effect of said stimulation. For example, to assess proximity to the target nerve, electrical energy is applied to the energy delivery device using a frequency that excites sensory nerves, typically 30-70 Hz with a current of up to 1 mA. To confirm that the probe is not in proximity to an untargeted nerve, motor nerve stimulation is performed typically at a frequency of 1-5 Hz and a current of 3-5 mA. As is well known in the art, various frequencies and voltages can be used to stimulate both sensory and motor nerves. Observation of said stimulation can take the form of visual, sensory, mechanical, or electrical detection of muscle activity, or the form of sensory or electrical detection of nociceptive or other sensory neural activity (e.g. temperature sensation). The electrical energy ("stimulation energy") applied during this step is beneficially capable of eliciting a response from a neural structure without damaging the neural structure. Using this step, it can be determined whether a target nerve or nerves has a function that would contraindicate its ablation or functional alteration. In one embodiment, the lack of a contraindication would lead to the step of delivering energy, whereas the presence of a contraindication would lead back to the step of inserting one or more probe assemblies, whereby the step of inserting a probe assembly includes modifying the position of a probe assembly within the body. Furthermore, in some embodiments, a method of this aspect of the present invention may comprise a step of stimulating neural tissue after a treatment procedure in order to determine the effectiveness of the treatment procedure. A stimulation step, as has been described, may be performed in a monopolar mode, wherein energy configured to stimulate a nerve is concentrated around a distal tip region of a single probe assembly in order to assess the proximity of neural tissue to that probe assembly. Alternatively, a stimulation procedure may be performed in a bipolar mode, wherein energy configured to stimulate a nerve is preferentially concentrated between the distal tip regions of two probe assemblies, thus allowing a user to detect neural tissue located substantially between the probe assemblies. In general, it may be beneficial to perform a stimulation step employing a similar probe assembly configuration as will be used to deliver energy. Thus, if energy will be delivered using a monopolar configuration, it may be beneficial to perform a stimulation step in a monopolar configuration as well. Similarly, if energy will be delivered using a bipolar configuration, it may be beneficial to perform a stimulation step in a bipolar configuration, as has been described.

As has been mentioned, a system of the present invention may be used to produce a relatively uniform lesion substantially between two probe assemblies 106 when operated in a bipolar mode. Oftentimes, uniform lesions may be contraindicated, such as in a case where a tissue to be treated is located closer to one energy delivery device 192 than to the other. In cases where a uniform lesion may be undesirable, using two or more cooled probe assemblies 106 in combination with a suitable feedback and control system may allow for the creation of lesions of varying size and shape. For example, preset temperature and/or power profiles that the procedure should follow may be programmed into a generator prior to commencement of a treatment procedure. These profiles may define parameters (these parameters would depend on certain tissue parameters, such as heat capacity, etc.) that should be used in order to create a lesion of a specific size and shape. These parameters may include, but are not limited to, maximum allowable temperature, ramp rate (i.e. how quickly the temperature is raised) and the rate of cooling flow, for each individual probe. Based on temperature or impedance measurements performed during the procedure, various parameters, such as power or cooling, may be modulated, in order to comply with the preset profiles, resulting in a lesion with the desired dimensions.

Similarly, it is to be understood that a uniform lesion can be created, using a system of the present invention, using many different pre-set temperature and/or power profiles which allow the thermal dose across the tissue to be as uniform as possible, and that the present invention is not limited in this regard.

It should be noted that the term radiopaque marker as used herein denotes any addition or reduction of material that increases or reduces the radiopacity of the device. Furthermore, the terms probe assembly, introducer, stylet etc. are not intended to be limiting and denote any medical and surgical tools that can be used to perform similar functions to those described. In addition, the invention is not limited to be used in the clinical applications disclosed herein, and other medical and surgical procedures wherein a device of the present invention would be useful are included within the scope of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:
1. An intradiscal probe assembly, comprising:
   first and second probes for treatment of a patients intervertebral disc, the intervertebral disc including a nucleus pulposus bounded by an annulus fibrosus, each of the first and second probes comprising:
      an elongate shaft for surgical insertion to a treatment site for the annulus fibrosus, the elongate shaft comprising a proximal portion and a distal portion;
      an electrically-conductive energy delivery device secured at a distal-most end of the distal portion of the elongate shaft, the energy delivery device and the elongate shaft comprising equal inner and outer diameters so as to define an internal lumen having a constant diameter; and
      an impedance measuring tip secured at a distal-most end of the energy delivery device, the impedance measuring tip being electrically and spatially separate from the energy delivery device,
   wherein the energy delivery devices of the firstand second probes deliver energy in a bipolar mode between the distal portions thereof through the annulus fibrosus so as to create a lesion within the annulus fibrosus.

2. The intradiscal probe assembly of claim 1, wherein the intradiscal probe is connected to a power source.

3. The intradiscal probe assembly of claim 2, wherein the power source comprises a control unit for regulating the power transmitted by the impedance measuring tip.

4. The intradiscal probe assembly of claim 1, wherein the energy delivery device comprises an electrode.

5. The intradiscal probe assembly of claim 1, wherein an electrical current conducted between the intradiscal probe and the second probe has a frequency within the radio frequency range.

6. The intradiscal probe of claim 1, further comprising an insulating material arranged between the energy delivery device and the impedance measuring tip.

7. An intradiscal probe assembly for treatment of a patient's intervertebral disc, the intervertebral disc including a nucleus pulposus bounded by an annulus fibrosus, the intradiscal probe assembly comprising:
   first and second probes each comprising:
      an elongate shaft for surgical insertion to a treatment site for the annulus fibrosus, the elongate shaft having a proximal portion and a distal portion;
      an energy delivery device secured at a distal-most end of the distal portion of the elongate shaft, the energy delivery device and the elongate shaft comprising equal inner and outer diameters so as to define an internal lumen having a constant diameter; and
      an impedance measuring tip secured at a distal-most end of the energy delivery device, the impedance measuring tip being electrically and spatially separate from the energy delivery device,
   wherein the energy delivery devices of the first and second probes selectively deliver energy to the annulus fibrosus in a desired direction.

8. The intradiscal probe assembly of claim 7, wherein the intradiscal probe is connected to a power source.

9. The intradiscal probe assembly of claim 8, wherein the power source comprises a control unit for regulating the power transmitted by the impedance measuring tip.

10. The intradiscal probe assembly of claim 7, wherein the energy delivery device comprises an electrode.

11. The intradiscal probe assembly of claim 7, wherein an electrical current conducted between the intradiscal probe and a second probe has a frequency within the radio frequency range.

12. The intradiscal probe of claim 7, further comprising an insulating material arranged between the energy delivery device and the impedance measuring tip.

13. An intradiscal probe assembly for treatment of a patients intervertebral disc, the intervertebral disc including a nucleus pulposus bounded by an annulus fibrosus, the intradiscal probe assembly comprising:
   a first elongate probe for surgical insertion to a treatment site for the annulus fibrosus, the first elongate probe having a proximal portion and a distal portion;
   a second elongate probe for surgical insertion to the treatment site for the annulus fibrosus, the second elongate probe having a proximal portion and a distal portion;
   a first energy delivery device secured at a distal-most end of the distal portion of the first elongate probe;
   a second energy delivery device secured at a distal-most end of the distal portion of the second elongate probe, the first and second energy delivery devices and the first and second elongate probes comprising equal inner and outer diameters, respectively, so as to define an internal lumen having a constant diameter;
   an impedance measuring tip secured at a distal-most end of each of the first energy delivery device and the second energy delivery device, the impedance measuring tip being electrically and spatially separate from the energy delivery device,
   wherein the first and second energy delivery devices deliver energy in a bipolar mode between the distal portions of the first and second elongate probes through the annulus fibrosus so as to create a lesion within the annulus fibrosus.

14. The intradiscal probe assembly of claim 13, wherein the intradiscal probe is connected to a power source.

15. The intradiscal probe assembly of claim 14, wherein the power source comprises a control unit for egulating the power transmitted by the impedance measuring tip.

16. The intradiscal probe assembly of claim 13, wherein the energy delivery device comprises an electrode.

17. The intradiscal probe assembly of claim 13, wherein an electrical current conducted between the intradiscal probe and the second probe has a frequency within the radio frequency range.

18. The intradiscal probe of claim 13, further comprising an insulating material arranged between at least one of the first energy delivery device and the impedance measuring tip or the second energy delivery device and the impedance measuring tip.

* * * * *